(12) United States Patent
Peri et al.

(10) Patent No.: US 8,822,413 B2
(45) Date of Patent: Sep. 2, 2014

(54) BIFUNCTIONAL HORMONE HAVING ALPHA-MSH ACTIVITY AND NATRIURETIC PEPTIDE ACTIVITY AND USES THEREOF

(75) Inventors: Krishna G. Peri, Montreal (CA); Abdelkrim Habi, Pierrefonds (CA)

(73) Assignee: Theratechnologies Inc., Monteal, Quebec (CA)

( * ) Notice: Subject to any disclaimer, the term of this patent is extended or adjusted under 35 U.S.C. 154(b) by 1170 days.

(21) Appl. No.: 12/168,513

(22) Filed: Jul. 7, 2008

(65) Prior Publication Data

US 2009/0011997 A1 Jan. 8, 2009

Related U.S. Application Data

(60) Provisional application No. 60/948,292, filed on Jul. 6, 2007.

(51) Int. Cl.
*A61K 38/22* (2006.01)
*A61K 38/16* (2006.01)
*A61K 38/00* (2006.01)

(52) U.S. Cl.
USPC ......... 514/5.3; 514/15.4; 514/15.7; 514/21.3; 530/324

(58) Field of Classification Search
None
See application file for complete search history.

(56) References Cited

U.S. PATENT DOCUMENTS

| 2004/0142893 | A1* | 7/2004 | Ikeda et al. | 514/44 |
| 2006/0094652 | A1* | 5/2006 | Levy et al. | 514/12 |

FOREIGN PATENT DOCUMENTS

| WO | WO 90/00561 | 1/1990 |
| WO | WO 2004/011498 | 2/2004 |
| WO | WO-2005077072 | 8/2005 |
| WO | WO-2005077094 | 8/2005 |
| WO | WO-2006066024 | 6/2006 |
| WO | WO-2007022123 | 2/2007 |
| WO | WO-2008021560 | 2/2008 |

OTHER PUBLICATIONS

Levin et al. 1998. NEJM. 339:321.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston.*
Wang et al 2001. J. Biol Chem. 276:49213-49220.*
MedlinePlus, Acute kidney failure (http://www.nim.nih.gov/medlineplus/ency/article/000501.htm, downloaded Sep. 2, 2010).*
Fung et al., "Design of Cyclic and Other Templates for Potent and Selective Peptide Alpha-MSH Analogues," Current Opinion in Chemical Biology, 2005, 9:352-358.
Ni et al., "Prevention of Reflex Natriuresis After Acute Unilateral Nephrectomy by Melanocortin Receptor Antagonists," American Journal of Physiology (Regulatory, Integrative and Comparative Physiology), 1998, 274:R931-R938.
Wang et al., "Overexpression and Purification of Recombinant Atrial Natriuretic Peptide Using Hybrid Fusion Protein REF-ANP in *Escherichia coli*," Protein Expression & Purification, 2003, 28:49-56.
Baumanis et al., Synthesis of Recombinant Atrial Natriuretic Peptide (rANP) Using Hybrid Fusion Protein-Phage fr Coat/ANP (CP/ANP), Peptides, 1997, vol. 18, No. 8, pp. 1229-1235, ISSN: 0196-9781.
Supplementary European Search Report in respect of corresponding EP Application No. EP 08783182, 2010.

* cited by examiner

*Primary Examiner* — Shulamith H Shafer
(74) *Attorney, Agent, or Firm* — Fish & Richardson P.C.

(57) ABSTRACT

A bifunctional hormone exhibiting an alpha-MSH activity and a natriuretic peptide activity is described. The bifunctional hormone comprises for example a first domain having alpha-MSH related hormonal activity covalently linked to a second domain having natriuretic peptide related hormonal activity. The bifunctional hormone of the present invention is useful for example for the prevention and/or treatment of renal related diseases or conditions, such as acute renal failure (ARF) or acute kidney injury (AKI).

25 Claims, 4 Drawing Sheets

A

B

SEQUENCE LISTING

```
<160> NUMBER OF SEQ ID NOS: 72

<210> SEQ ID NO 1
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
```

-continued

```
<400> SEQUENCE: 1

Ser Tyr Ser Met Glu His Phe Arg Trp Gly Lys Pro Val
1               5                   10

<210> SEQ ID NO 2
<211> LENGTH: 28
<212> TYPE: PRT
<213> ORGANISM: Homo sapiens
<220> FEATURE:
<221> NAME/KEY: DISULFID
<222> LOCATION: (7)..(23)

<400> SEQUENCE: 2

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 3
<211> LENGTH: 32
<212> TYPE: PRT
<213> ORGANISM: Homo sapiens
<220> FEATURE:
<221> NAME/KEY: DISULFID
<222> LOCATION: (11)..(27)

<400> SEQUENCE: 3

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 4
<211> LENGTH: 32
<212> TYPE: PRT
<213> ORGANISM: Homo sapiens
<220> FEATURE:
<221> NAME/KEY: DISULFID
<222> LOCATION: (10)..(26)

<400> SEQUENCE: 4

Ser Pro Lys Met Val Gln Gly Ser Gly Cys Pro Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 5
<211> LENGTH: 22
<212> TYPE: PRT
<213> ORGANISM: Homo sapiens
<220> FEATURE:
<221> NAME/KEY: DISULFID
<222> LOCATION: (6)..(22)

<400> SEQUENCE: 5

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 6
<211> LENGTH: 4
<212> TYPE: PRT
<213> ORGANISM: Artificial Sequence
```

```
<220> FEATURE:
<223> OTHER INFORMATION: Peptide derived from alpha-MSH
<220> FEATURE:
<221> NAME/KEY: MISC_FEATURE
<222> LOCATION: (2)..(2)
<223> OTHER INFORMATION: Xaa at position 2 = D-Phenylalanine

<400> SEQUENCE: 6

His Xaa Arg Trp
1

<210> SEQ ID NO 7
<211> LENGTH: 8
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine

<400> SEQUENCE: 7

His Xaa Arg Trp Gly Lys Pro Met
1               5

<210> SEQ ID NO 8
<211> LENGTH: 4
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine

<400> SEQUENCE: 8

His Xaa Arg Trp
1

<210> SEQ ID NO 9
<211> LENGTH: 5
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine

<400> SEQUENCE: 9

His Xaa Arg Trp Gly
1               5

<210> SEQ ID NO 10
<211> LENGTH: 7
<212> TYPE: PRT
```

```
<213> ORGANISM: Artificial Sequence
<220> FEATURE:
<223> OTHER INFORMATION: Peptide derived from alpha-MSH
<220> FEATURE:
<221> NAME/KEY: MISC_FEATURE
<222> LOCATION: (4)..(4)
<223> OTHER INFORMATION: Xaa at position 4 = D-phenylalanine

<400> SEQUENCE: 10

Met Glu His Xaa Arg Trp Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Peptide derived from alpha-MSH

<400> SEQUENCE: 11

Met Glu His Phe Arg Trp Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: MOD_RES
<222> LOCATION: (8)..(8)
<223> OTHER INFORMATION: Nle

<400> SEQUENCE: 12

His Xaa Arg Trp Gly Lys Pro Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION

<400> SEQUENCE: 13

His Phe Arg Trp Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
```

```
<400> SEQUENCE: 14

Glu His Phe Arg Trp Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa at position 3 = D-phenylalanine

<400> SEQUENCE: 15

Glu His Xaa Arg Trp Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 is L-phenylalanine or
      D-phenylalanine
<220> FEATURE:
<221> NAME/KEY: MISC_FEATURE
<222> LOCATION: (8)..(8)
<223> OTHER INFORMATION: Xaa at position 8 is methionine, valine or
      norleucine

<400> SEQUENCE: 16

His Xaa Arg Trp Gly Lys Pro Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MISC_FEATURE
<222> LOCATION: (3)..(3)
<223> OTHER INFORMATION: Xaa at position 3 is L-phenylalanine or
      D-phenylalanine

<400> SEQUENCE: 17

Glu His Xaa Arg Trp Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Peptide derived from alpha-MSH
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 is L-phenylalanine or
      D-phenylalanine

<400> SEQUENCE: 18

His Xaa Arg Trp Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa at position 3 is L-phenylalanine or
      D-phenylalanine

<400> SEQUENCE: 19

Glu His Xaa Arg Trp
1               5

<210> SEQ ID NO 20
<211> LENGTH: 4
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MISC_FEATURE
<222> LOCATION: (2)..(2)
<223> OTHER INFORMATION: Xaa at position 2 is L-phenylalanine or
      D-phenylalanine

<400> SEQUENCE: 20

His Xaa Arg Trp
1

<210> SEQ ID NO 21
<211> LENGTH: 4
<212> TYPE: PRT
<213> ORGANISM: Artificial Sequence
<220> FEATURE:
<223> OTHER INFORMATION: Peptide derived from alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 is L-phenylalanine or
      D-phenylalanine

<400> SEQUENCE: 21

His Xaa Arg Trp
1

<210> SEQ ID NO 22
```

```
<211> LENGTH: 15
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (2)..(13)

<400> SEQUENCE: 22

Met Cys His Phe Gly Gly Arg Met Asp Arg Ile Ser Cys Tyr Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(13)
<220> FEATURE:
<221> NAME/KEY: MOD_RES
<222> LOCATION: (8)..(8)
<223> OTHER INFORMATION: Nle

<400> SEQUENCE: 23

Xaa Cys His Phe Gly Gly Arg Xaa Asp Arg Ile Ser Cys Tyr Arg
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (1)..(17)

<400> SEQUENCE: 24

Cys Phe Gly Gly Arg Met Asp Arg Ile Gly Ala Gln Ser Gly Leu Gly
1               5                   10                  15

Cys Asn Ser Phe Arg Tyr
            20

<210> SEQ ID NO 25
<211> LENGTH: 22
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (1)..(17)
<220> FEATURE:
<221> NAME/KEY: MOD_RES
<222> LOCATION: (6)..(6)
<223> OTHER INFORMATION: Nle

<400> SEQUENCE: 25

Cys Phe Gly Gly Arg Xaa Asp Arg Ile Gly Ala Gln Ser Gly Leu Gly
1               5                   10                  15

Cys Asn Ser Phe Arg Tyr
            20
```

```
<210> SEQ ID NO 26
<211> LENGTH: 26
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (5)..(21)

<400> SEQUENCE: 26

Arg Arg Ser Ser Cys Phe Gly Gly Arg Met Asp Arg Ile Gly Ala Gln
1               5                   10                  15

Ser Gly Leu Gly Cys Asn Ser Phe Arg Tyr
            20                  25

<210> SEQ ID NO 27
<211> LENGTH: 32
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (10)..(26)

<400> SEQUENCE: 27

Ser Pro Lys Met Val Gln Gly Ser Gly Cys Pro Gly Arg Lys Met Asp
1               5                   10                  15

Arg Ile Ser Ser Ser Gly Leu Gly Cys Lys Val Leu Arg Arg His
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Peptide derived from a natriuretic peptide
<220> FEATURE:
<221> NAME/KEY: DISULFID
<222> LOCATION: (9)..(25)

<400> SEQUENCE: 28

Pro Lys Pro Val Gln Gly Ser Gly Cys Pro Gly Arg Lys Met Asp Arg
1               5                   10                  15

Ile Ser Ser Ser Gly Leu Gly Cys Lys Val Leu Arg Arg His
            20                  25                  30

<210> SEQ ID NO 29
<211> LENGTH: 19
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(2)
<223> OTHER INFORMATION: The glutamic acid residue at position 2 forms a
      lactam bridge with the lysine residue at position 13
<220> FEATURE:
<221> NAME/KEY: MOD_RES
<222> LOCATION: (8)..(8)
<223> OTHER INFORMATION: Nle
<220> FEATURE:
```

<221> NAME/KEY: MISC_FEATURE
<222> LOCATION: (13)..(13)
<223> OTHER INFORMATION: The lysine residue at position 13 forms a
      lactam bridge with the glutamic acid residue at position 2
<220> FEATURE:
<221> NAME/KEY: MISC_FEATURE
<222> LOCATION: (17)..(17)
<223> OTHER INFORMATION: Xaa at position 17 = D-phenylalanine
<220> FEATURE:
<221> NAME/KEY: MOD_RES
<222> LOCATION: (19)..(19)
<223> OTHER INFORMATION: AMIDATION

<400> SEQUENCE: 29

Xaa Glu His Phe Gly Gly Arg Xaa Asp Arg Ile Ser Lys Tyr Arg His
1               5                   10                  15

Xaa Arg Trp

<210> SEQ ID NO 30
<211> LENGTH: 22
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (9)..(20)
<220> FEATURE:
<221> NAME/KEY: MOD_RES
<222> LOCATION: (22)..(22)
<223> OTHER INFORMATION: AMIDATION

<400> SEQUENCE: 30

His Xaa Arg Trp Gly Lys Pro Met Glu His Phe Gly Gly Arg Met Asp
1               5                   10                  15

Arg Ile Ser Lys Tyr Arg
            20

<210> SEQ ID NO 31
<211> LENGTH: 22
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (9)..(20)
<220> FEATURE:
<221> NAME/KEY: MOD_RES
<222> LOCATION: (22)..(22)
<223> OTHER INFORMATION: AMIDATION

<400> SEQUENCE: 31

His Xaa Arg Trp Gly Lys Pro Met Cys His Phe Gly Gly Arg Met Asp
1               5                   10                  15

Arg Ile Ser Cys Tyr Arg
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(13)
<220> FEATURE:
<221> NAME/KEY: MOD_RES
<222> LOCATION: (8)..(8)
<223> OTHER INFORMATION: Nle

<400> SEQUENCE: 32

Xaa Cys His Phe Gly Gly Arg Xaa Asp Arg Ile Ser Cys Tyr Arg His
1               5                   10                  15

Phe Arg Trp

<210> SEQ ID NO 33
<211> LENGTH: 30
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (9)..(25)
<220> FEATURE:
<221> NAME/KEY: MOD_RES
<222> LOCATION: (30)..(30)
<223> OTHER INFORMATION: AMIDATION

<400> SEQUENCE: 33

His Xaa Arg Trp Gly Lys Pro Met Cys Phe Gly Gly Arg Met Asp Arg
1               5                   10                  15

Ile Gly Ala Gln Ser Gly Leu Gly Cys Asn Ser Phe Arg Tyr
            20                  25                  30

<210> SEQ ID NO 34
<211> LENGTH: 22
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: DISULFID
<222> LOCATION: (9)..(20)
<220> FEATURE:
<221> NAME/KEY: MOD_RES
<222> LOCATION: (15)..(15)
<223> OTHER INFORMATION: Nle
<220> FEATURE:
<221> NAME/KEY: MOD_RES
<222> LOCATION: (22)..(22)
<223> OTHER INFORMATION: AMIDATION

<400> SEQUENCE: 34

His Xaa Arg Trp Gly Lys Pro Xaa Cys His Phe Gly Gly Arg Xaa Asp
1               5                   10                  15

Arg Ile Ser Cys Tyr Arg
            20

<210> SEQ ID NO 35
<211> LENGTH: 30
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: MOD_RES
<222> LOCATION: (8)..(8)
<223> OTHER INFORMATION: Nle
<220> FEATURE:
<221> NAME/KEY: DISULFID
<222> LOCATION: (9)..(25)
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (30)..(30)
<223> OTHER INFORMATION: AMIDATION

<400> SEQUENCE: 35

His Xaa Arg Trp Gly Lys Pro Xaa Cys Phe Gly Gly Arg Xaa Asp Arg
1               5                   10                  15

Ile Gly Ala Gln Ser Gly Leu Gly Cys Asn Ser Phe Arg Tyr
            20                  25                  30

<210> SEQ ID NO 36
<211> LENGTH: 33
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: DISULFID
<222> LOCATION: (12)..(28)
<220> FEATURE:
<221> NAME/KEY: MOD_RES
<222> LOCATION: (33)..(33)
<223> OTHER INFORMATION: AMIDATION

<400> SEQUENCE: 36

Met Glu His Phe Arg Trp Gly Arg Arg Ser Ser Cys Phe Gly Gly Arg
1               5                   10                  15

```
Met Asp Arg Ile Gly Ala Gln Ser Gly Leu Gly Cys Asn Ser Phe Arg
            20                  25                  30

Tyr

<210> SEQ ID NO 37
<211> LENGTH: 33
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MISC_FEATURE
<222> LOCATION: (4)..(4)
<223> OTHER INFORMATION: Xaa at position 4 = D-phenylalanine
<220> FEATURE:
<221> NAME/KEY: DISULFID
<222> LOCATION: (12)..(28)
<220> FEATURE:
<221> NAME/KEY: MOD_RES
<222> LOCATION: (33)..(33)
<223> OTHER INFORMATION: AMIDATION

<400> SEQUENCE: 37

Met Glu His Xaa Arg Trp Gly Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 38
<211> LENGTH: 31
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (10)..(26)
<220> FEATURE:
<221> NAME/KEY: MOD_RES
<222> LOCATION: (31)..(31)
<223> OTHER INFORMATION: AMIDATION

<400> SEQUENCE: 38

His Phe Arg Trp Gly Arg Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (10)..(26)
```

```
<220> FEATURE:
<221> NAME/KEY: MOD_RES
<222> LOCATION: (31)..(31)
<223> OTHER INFORMATION: AMIDATION

<400> SEQUENCE: 39

His Xaa Arg Trp Gly Arg Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: DISULFID
<222> LOCATION: (7)..(23)
<220> FEATURE:
<221> NAME/KEY: MISC_FEATURE
<222> LOCATION: (30)..(30)
<223> OTHER INFORMATION: Xaa at position 30 = D-phenylalanine
<220> FEATURE:
<221> NAME/KEY: MOD_RES
<222> LOCATION: (32)..(32)
<223> OTHER INFORMATION: AMIDATION

<400> SEQUENCE: 40

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr His Xaa Arg Trp
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (11)..(27)
<220> FEATURE:
<221> NAME/KEY: MOD_RES
<222> LOCATION: (32)..(32)
<223> OTHER INFORMATION: AMIDATION

<400> SEQUENCE: 41

Glu His Phe Arg Trp Gly Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (3)..(3)
<223> OTHER INFORMATION: Xaa at position 3 = D-phenylalanine
<220> FEATURE:
<221> NAME/KEY: DISULFID
<222> LOCATION: (11)..(27)
<220> FEATURE:
<221> NAME/KEY: MOD_RES
<222> LOCATION: (32)..(32)
<223> OTHER INFORMATION: AMIDATION

<400> SEQUENCE: 42

Glu His Xaa Arg Trp Gly Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 43
<211> LENGTH: 29
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (8)..(24)
<220> FEATURE:
<221> NAME/KEY: MOD_RES
<222> LOCATION: (29)..(29)
<223> OTHER INFORMATION: AMIDATION

<400> SEQUENCE: 43

His Arg Trp Gly Lys Pro Met Cys Phe Gly Gly Arg Met Asp Arg Ile
1               5                   10                  15

Gly Ala Gln Ser Gly Leu Gly Cys Asn Ser Phe Arg Tyr
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (9)..(22)
<220> FEATURE:
<221> NAME/KEY: MOD_RES
<222> LOCATION: (27)..(27)
<223> OTHER INFORMATION: AMIDATION

<400> SEQUENCE: 44

His Xaa Arg Trp Gly Lys Pro Met Cys Phe Gly Gly Arg Met Gly Ala
1               5                   10                  15

Gln Ser Gly Leu Gly Cys Asn Ser Phe Arg Tyr
            20                  25

<210> SEQ ID NO 45
```

```
<211> LENGTH: 36
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (14)..(30)
<220> FEATURE:
<221> NAME/KEY: MOD_RES
<222> LOCATION: (36)..(36)
<223> OTHER INFORMATION: AMIDATION

<400> SEQUENCE: 45

His Xaa Arg Trp Ser Pro Lys Met Val Gln Gly Ser Gly Cys Pro Gly
1               5                   10                  15

Arg Lys Met Asp Arg Ile Ser Ser Ser Ser Gly Leu Gly Cys Lys Val
            20                  25                  30

Leu Arg Arg His
        35

<210> SEQ ID NO 46
<211> LENGTH: 36
<212> TYPE: PRT
<213> ORGANISM: Artificial Sequence
<220> FEATURE:
<223> OTHER INFORMATION: Synthetic bifunctional hormone
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa at position 2 = D-phenylalanine
<220> FEATURE:
<221> NAME/KEY: DISULFID
<222> LOCATION: (14)..(30)
<220> FEATURE:
<221> NAME/KEY: MOD_RES
<222> LOCATION: (36)..(36)
<223> OTHER INFORMATION: AMIDATION

<400> SEQUENCE: 46

His Xaa Arg Trp Gly Pro Lys Pro Val Gln Gly Ser Gly Cys Pro Gly
1               5                   10                  15

Arg Lys Met Asp Arg Ile Ser Ser Ser Ser Gly Leu Gly Cys Lys Val
            20                  25                  30

Leu Arg Arg His
        35

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is Met or is absent
<220> FEATURE:
<221> NAME/KEY: MISC_FEATURE
```

<222> LOCATION: (2)..(2)
<223> OTHER INFORMATION: Xaa at position 2 is Glu or is absent
<220> FEATURE:
<221> NAME/KEY: MISC_FEATURE
<222> LOCATION: (4)..(4)
<223> OTHER INFORMATION: Xaa at position 4 is L-Phe or D-Phe
<220> FEATURE:
<221> NAME/KEY: MISC_FEATURE
<222> LOCATION: (7)..(7)
<223> OTHER INFORMATION: Xaa at position 7 is Gly or is absent
<220> FEATURE:
<221> NAME/KEY: MISC_FEATURE
<222> LOCATION: (8)..(8)
<223> OTHER INFORMATION: Xaa at position 8 is Lys or is absent
<220> FEATURE:
<221> NAME/KEY: MISC_FEATURE
<222> LOCATION: (9)..(9)
<223> OTHER INFORMATION: Xaa at position 9 is Pro or is absent
<220> FEATURE:
<221> NAME/KEY: MISC_FEATURE
<222> LOCATION: (10)..(10)
<223> OTHER INFORMATION: Xaa at position 10 is Met, Val, Nle or is
      absent

<400> SEQUENCE: 47

Xaa Xaa His Xaa Arg Trp Xaa Xaa Xaa Xaa
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is L-Phe or D-Phe
<220> FEATURE:
<221> NAME/KEY: MISC_FEATURE
<222> LOCATION: (8)..(8)
<223> OTHER INFORMATION: Xaa at position 8 is Met, Val or Nle

<400> SEQUENCE: 48

His Xaa Arg Trp Gly Lys Pro Xaa
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is L-Phe or D-Phe

<400> SEQUENCE: 49

His Xaa Arg Trp Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position 3 is L-Phe or D-Phe

```
<400> SEQUENCE: 50

Glu His Xaa Arg Trp Gly
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe

<400> SEQUENCE: 51

His Xaa Arg Trp Gly Lys Pro Val
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe

<400> SEQUENCE: 52

His Xaa Arg Trp Gly Lys Pro Met
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: MOD_RES
<222> LOCATION: (8)..(8)
<223> OTHER INFORMATION: Nle

<400> SEQUENCE: 53

His Xaa Arg Trp Gly Lys Pro Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe

<400> SEQUENCE: 54

His Xaa Arg Trp Gly Lys Pro
1               5

<210> SEQ ID NO 55
```

-continued

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe

<400> SEQUENCE: 55

His Xaa Arg Trp Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide

<400> SEQUENCE: 56

Glu His Phe Arg Trp
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position 3 is D-Phe

<400> SEQUENCE: 57

Glu His Xaa Arg Trp Gly
1               5

<210> SEQ ID NO 58
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Xaa at positions 1 to 6 correspond to: Ser-
      Leu-Arg-Arg-Ser-Ser; Arg-Arg-Ser-Ser wherein Xaa at positions 1
      and 2 are absent; Met wherein Xaa at positions 1 to 5 are absent;
      or Nle wherein Xaa at positions 1 to 5 are absent
<220> FEATURE:
<221> NAME/KEY: MISC_FEATURE
<222> LOCATION: (8)..(8)
<223> OTHER INFORMATION: Xaa at position 8 is His or is absent
<220> FEATURE:
<221> NAME/KEY: MISC_FEATURE
<222> LOCATION: (13)..(13)
<223> OTHER INFORMATION: Xaa at position 13 is Met or Nle
<220> FEATURE:
<221> NAME/KEY: MISC_FEATURE
<222> LOCATION: (17)..(29)
<223> OTHER INFORMATION: Xaa at position 17 to 29 corresponds to: Ser-
      Cys-Tyr-Arg wherein Xaa at positions 21 to 29 are absent; or
      Gly-Ala-Gln-Ser-Gly-Leu-Gly-Cys-Asn-Ser-Phe-Arg-Tyr
<220> FEATURE:
<221> NAME/KEY: DISULFID
<222> LOCATION: (7)..(18)
<223> OTHER INFORMATION: When Xaa at position 17 to 29 corresponds to:
      Ser-Cys-Tyr-Arg and Xaa at positions 21 to 29 are absent, Cys at
      position 7 and Cys at position 18 are linked via a disulfide
```

```
            bridge
<220> FEATURE:
<221> NAME/KEY: DISULFID
<222> LOCATION: (7)..(24)
<223> OTHER INFORMATION: When Xaa at position 17 to 29 corresponds to:
      Gly-Ala-Gln-Ser-Gly-Leu-Gly-Cys-Asn-Ser-Phe-Arg-Tyr, Cys at
      position 7 and Cys at position 24 are linked via a disulfide
      bridge

<400> SEQUENCE: 58

Xaa Xaa Xaa Xaa Xaa Xaa Cys Xaa Phe Gly Gly Arg Xaa Asp Arg Ile
1               5                   10                  15

Xaa Xaa Xaa Xaa Xaa Xaa Xaa Xaa Xaa Xaa Xaa Xaa Xaa
            20                  25

<210> SEQ ID NO 59
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (7)..(23)

<400> SEQUENCE: 59

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 60
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(18)

<400> SEQUENCE: 60

Met Cys Phe Gly Gly Arg Met Asp Arg Ile Gly Ala Gln Ser Gly Leu
1               5                   10                  15

Gly Cys Asn Ser Phe Arg Tyr
            20

<210> SEQ ID NO 61
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: DISULFID
<222> LOCATION: (9)..(20)

<400> SEQUENCE: 61

His Xaa Arg Trp Gly Lys Pro Met Cys His Phe Gly Gly Arg Met Asp
1               5                   10                  15

Arg Ile Ser Cys Tyr Arg
            20
```

```
<210> SEQ ID NO 62
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: DISULFID
<222> LOCATION: (9)..(25)

<400> SEQUENCE: 62

His Xaa Arg Trp Gly Lys Pro Met Cys Phe Gly Gly Arg Met Asp Arg
1               5                   10                  15

Ile Gly Ala Gln Ser Gly Leu Gly Cys Asn Ser Phe Arg Tyr
            20                  25                  30

<210> SEQ ID NO 63
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: MOD_RES
<222> LOCATION: (8)..(8)
<223> OTHER INFORMATION: Nle
<220> FEATURE:
<221> NAME/KEY: DISULFID
<222> LOCATION: (9)..(20)
<220> FEATURE:
<221> NAME/KEY: MOD_RES
<222> LOCATION: (15)..(15)
<223> OTHER INFORMATION: Nle

<400> SEQUENCE: 63

His Xaa Arg Trp Gly Lys Pro Xaa Cys His Phe Gly Gly Arg Xaa Asp
1               5                   10                  15

Arg Ile Ser Cys Tyr Arg
            20

<210> SEQ ID NO 64
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: MOD_RES
<222> LOCATION: (8)..(8)
<223> OTHER INFORMATION: Nle
<220> FEATURE:
<221> NAME/KEY: DISULFID
<222> LOCATION: (9)..(25)
<220> FEATURE:
<221> NAME/KEY: MOD_RES
<222> LOCATION: (14)..(14)
<223> OTHER INFORMATION: Nle

<400> SEQUENCE: 64

His Xaa Arg Trp Gly Lys Pro Xaa Cys Phe Gly Gly Arg Xaa Asp Arg
```

Ile Gly Ala Gln Ser Gly Leu Gly Cys Asn Ser Phe Arg Tyr
        20                  25                  30

<210> SEQ ID NO 65
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (12)..(28)

<400> SEQUENCE: 65

Met Glu His Phe Arg Trp Gly Arg Arg Ser Ser Cys Phe Gly Gly Arg
1               5                   10                  15

Met Asp Arg Ile Gly Ala Gln Ser Gly Leu Gly Cys Asn Ser Phe Arg
            20                  25                  30

Tyr

<210> SEQ ID NO 66
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (10)..(26)

<400> SEQUENCE: 66

His Phe Arg Trp Gly Arg Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 67
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at position 2 is D-Phe
<220> FEATURE:
<221> NAME/KEY: DISULFID
<222> LOCATION: (10)..(26)

<400> SEQUENCE: 67

His Xaa Arg Trp Gly Arg Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (7)..(23)
<220> FEATURE:

```
<221> NAME/KEY: MISC_FEATURE
<222> LOCATION: (30)..(30)
<223> OTHER INFORMATION: Xaa at position 30 is D-Phe

<400> SEQUENCE: 68

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr His Xaa Arg Trp
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position 3 is D-Phe
<220> FEATURE:
<221> NAME/KEY: DISULFID
<222> LOCATION: (11)..(27)

<400> SEQUENCE: 69

Glu His Xaa Arg Trp Gly Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(13)
<223> OTHER INFORMATION: The Glu residue at position 2 and the Lys
      residue at position 13 are linked by a lactam bridge
<220> FEATURE:
<221> NAME/KEY: MOD_RES
<222> LOCATION: (8)..(8)
<223> OTHER INFORMATION: Nle

<400> SEQUENCE: 70

Xaa Glu His Phe Gly Gly Arg Xaa Asp Arg Ile Ser Lys Tyr Arg
1               5                   10                  15

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
```

-continued

```
<223> OTHER INFORMATION: Xaa at positions 1 to 6 correspond to: Ser-
      Leu-Arg-Arg-Ser-Ser; Arg-Arg-Ser-Ser wherein Xaa at positions 1
      and 2 are absent; Met wherein Xaa at positions 1 to 5 are absent;
      or Nle wherein Xaa at positions 1 to 5 are absent
<220> FEATURE:
<221> NAME/KEY: MISC_FEATURE
<222> LOCATION: (7)..(7)
<223> OTHER INFORMATION: Xaa at position 7 is Asp or Glu
<220> FEATURE:
<221> NAME/KEY: MISC_FEATURE
<222> LOCATION: (7)..(18)
<223> OTHER INFORMATION: The Asp or Glu residue at position 7 and the
      Lys residue at position 18 are linked by a lactam bridge
<220> FEATURE:
<221> NAME/KEY: MISC_FEATURE
<222> LOCATION: (8)..(8)
<223> OTHER INFORMATION: Xaa at position 8 is His or is absent
<220> FEATURE:
<221> NAME/KEY: MISC_FEATURE
<222> LOCATION: (13)..(13)
<223> OTHER INFORMATION: Xaa at position 13 is Met or Nle

<400> SEQUENCE: 71

Xaa Xaa Xaa Xaa Xaa Xaa Xaa Xaa Phe Gly Gly Arg Xaa Asp Arg Ile
1               5                   10                  15

Ser Lys Tyr Arg
            20

<210> SEQ ID NO 72
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Xaa at positions 1 to 6 correspond to: Ser-Leu-
      Arg-Arg-Ser-Ser; Arg-Arg-Ser-Ser wherein Xaa at positions 1 and 2
      are absent; Met wherein Xaa at positions 1 to 5 are absent; or
      Nle wherein Xaa at positions 1 to 5 are absent
<220> FEATURE:
<221> NAME/KEY: MISC_FEATURE
<222> LOCATION: (7)..(7)
<223> OTHER INFORMATION: Xaa at position 7 is Asp, Glu or Cys
<220> FEATURE:
<221> NAME/KEY: MISC_FEATURE
<222> LOCATION: (7)..(18)
<223> OTHER INFORMATION: When Xaa at position 7 is Asp or Glu and Xaa at
      position 18 is Lys, the Asp or Glu residue at position 7 and the
      Lys residue at position 18 are linked by a lactam bridge
<220> FEATURE:
<221> NAME/KEY: MISC_FEATURE
<222> LOCATION: (8)..(8)
<223> OTHER INFORMATION: Xaa at position 8 is His or is absent
<220> FEATURE:
<221> NAME/KEY: MISC_FEATURE
<222> LOCATION: (13)..(13)
<223> OTHER INFORMATION: Xaa at position 13 is Met or Nle
<220> FEATURE:
<221> NAME/KEY: MISC_FEATURE
<222> LOCATION: (17)..(29)
<223> OTHER INFORMATION: Xaa at position 17 to 29 corresponds to: Ser-
      Cys-Tyr-Arg or Ser-Lys-Tyr-Arg wherein Xaa at positions 21 to 29
      are absent; or Gly-Ala-Gln-Ser-Gly-Leu-Gly-Cys-Asn-Ser-Phe-Arg-Tyr
<220> FEATURE:
<221> NAME/KEY: DISULFID
<222> LOCATION: (7)..(18)
<223> OTHER INFORMATION: When Xaa at position 17 to 29 corresponds to:
      Ser-Cys-Tyr-Arg and Xaa at positions 21 to 29 are absent, Cys at
      position 7 and Cys at position 18 are linked via a disulfide
      bridge
<220> FEATURE:
<221> NAME/KEY: DISULFID
<222> LOCATION: (7)..(24)
<223> OTHER INFORMATION: When Xaa at position 17 to 29 corresponds to:
```

```
Gly-Ala-Gln-Ser-Gly-Leu-Gly-Cys-Asn-Ser-Phe-Arg-Tyr, Cys at
position 7 and Cys at position 24 are linked via a disulfide
bridge

<400> SEQUENCE: 72

Xaa Xaa Xaa Xaa Xaa Xaa Xaa Xaa Phe Gly Gly Arg Xaa Asp Arg Ile
1               5                   10                  15

Xaa Xaa Xaa Xaa Xaa Xaa Xaa Xaa Xaa Xaa Xaa Xaa Xaa
            20                  25
```

BIFUNCTIONAL HORMONE HAVING ALPHA-MSH ACTIVITY AND NATRIURETIC PEPTIDE ACTIVITY AND USES THEREOF

CROSS REFERENCE TO RELATED APPLICATIONS

This application claims the benefit, under 35 U.S.C. §119 (e), of U.S. Provisional Patent Application Ser. No. 60/948,292 filed on Jul. 6, 2007, which is incorporated herein by reference in its entirety.

REFERENCE TO SEQUENCE LISTING

Pursuant to 37 C.F.R. 1.821(c), a sequence listing is submitted herewith as an ASCII compliant text file named "Sequence Listing.txt" which was created on Jun. 28, 2010 and has a size of 34,870 bytes. The content of the aforementioned file named "Sequence listing.txt" is hereby incorporated by reference in its entirety.

TECHNICAL FIELD

The present invention generally relates to novel compounds exhibiting hormonal activity and uses thereof, and particularly relates to novel compounds exhibiting bifunctional hormone activity, and uses thereof, such as for the prevention and/or treatment of renal related diseases or conditions, such as acute renal failure (ARF) or acute kidney injury (AKI).

BACKGROUND ART

Acute renal failure (ARF) is a sudden decline in renal function, over hours to days, manifested by a fall in urinary output. Nitrogenous waste products accumulate resulting in marked changes in electrolyte and fluid homoeostasis. Acute renal failure may result from a wide variety of clinical conditions or medications that induce ischemic injury or direct nephrotoxicity. Major surgical procedures, infections, shocks, postpartum hemorrhages and inadequate kidney perfusions may cause urinary output decrease. Acute renal failure is diagnosed by an increase in serum creatinine. In critically ill patients, the high catabolic state can lead to a rapid rise in nitrogenous waste products (reflected by rise in blood urea nitrogen (BUN)) and drastic shifts in fluid balance that leads to fluid overload.

There is a continued need to identify products and approaches for the prevention and treatment of renal related diseases or conditions, such as ARF.

The present description refers to a number of documents, the content of which is herein incorporated by reference in their entirety.

SUMMARY OF THE INVENTION

The present invention generally relates to novel compounds exhibiting hormonal activity and uses thereof, and particularly relates to novel compounds exhibiting bifunctional hormone activity, and uses thereof.

In a first aspect, the present invention provides a bifunctional hormone comprising:

(a) a first domain comprising an alpha-MSH peptide or a fragment, variant, or variant of a fragment thereof, said fragment, variant or variant of a fragment having alpha-MSH related hormonal activity; and (b) a second domain covalently linked to said first domain, said second domain comprising a natriuretic peptide or a fragment, variant, or variant of a fragment thereof, said fragment, variant or variant of a fragment having natriuretic peptide related hormonal activity.

In an embodiment, when the first domain is the alpha-MSH peptide of SEQ ID NO: 1; the second domain is the fragment, variant or variant of a fragment having natriuretic peptide related hormonal activity, and when the second domain is the natriuretic peptide of SEQ ID NOs: 2, 3, 4 or 5, the first domain is the fragment, variant or variant of a fragment having alpha-MSH related hormonal activity.

In an embodiment, the above-mentioned first domain comprises a fragment of at least 4 amino acids of the peptide of SEQ ID NO: 1, or a variant of the fragment having at least 75% homology with the fragment.

In another embodiment, the above-mentioned variant of an alpha-MSH peptide comprises an amino acid sequence having at least 75% homology with the amino acid sequence of SEQ ID NO: 1.

In an embodiment, the above-mentioned first domain comprises the amino acid sequence of Formula I (SEQ ID NO: 47):

$$X^2\text{-}H\text{-}X^1\text{-}R\text{-}W\text{-}X^3 \qquad (I)$$

wherein:
$X^1$ is L-Phe or D-Phe;
$X^2$ is E, M-E or is absent;
$X^3$ is G-K-P-$X^4$, G-K-P, G-K, G or is absent;
$X^4$ is M, V or Nle In an embodiment, the above-mentioned first domain comprises:

|      |                                       |                  |
|------|---------------------------------------|------------------|
| (i)  | 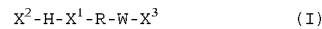 H-$X^1$-R-W-G-K-P-$X^4$;          | (SEQ ID NO: 48)  |
| (ii) | M-E-H-$X^1$-R-W-G;                    | (SEQ ID NO: 17)  |
| (iii)| H-$X^1$-R-W-G;                        | (SEQ ID NO: 49)  |
| (iv) | E-H-$X^1$-R-W-G;                      | (SEQ ID NO: 50)  |
| (v)  | H-$X^1$-R-W;                          | (SEQ ID NO: 20)  | or wherein $X^1$ is L-Phe or D-Phe, and $X^4$ is M, V or Nle.

In an embodiment, the above-mentioned first domain comprises:

|       |                     |                  |
|-------|---------------------|------------------|
| (i)   | H-f-R-W-G-K-P-V;    | (SEQ ID NO: 51)  |
| (ii)  | H-f-R-W-G-K-P-M;    | (SEQ ID NO: 52)  |
| (iii) | H-f-R-W-G-K-P-Nle;  | (SEQ ID NO: 53)  |
| (iv)  | H-f-R-W-G-K-P;      | (SEQ ID NO: 54)  |
| (v)   | M-E-H-F-R-W-G;      | (SEQ ID NO: 11)  |
| (vi)  | H-f-R-W-G;          | (SEQ ID NO: 55)  |
| (vii) | E-H-F-R-W;          | (SEQ ID NO: 56)  |
| (ix)  | E-H-f-R-W-G;        | (SEQ ID NO: 57)  | or

| (iv) | H-f-R-W; | (SEQ ID NO: 6) | wherein f is D-phenylalanine.

In an embodiment, the above-mentioned first domain consists of:

```
(i)    H-f-R-W-G-K-P-V;      (SEQ ID NO: 51)
(ii)   H-f-R-W-G-K-P-M;      (SEQ ID NO: 52)
(iii)  H-f-R-W-G-K-P-Nle;    (SEQ ID NO: 53)
(iv)   H-f-R-W-G-K-P;        (SEQ ID NO: 54)
(v)    M-E-H-F-R-W-G;        (SEQ ID NO: 11)
(vi)   H-f-R-W-G;            (SEQ ID NO: 55)
(vii)  E-H-F-R-W;            (SEQ ID NO: 56)
(ix)   E-H-f-R-W-G;          (SEQ ID NO: 57)
or
(iv)   H-f-R-W;              (SEQ ID NO: 6)
``` wherein f is D-phenylalanine.

In an embodiment, the above-mentioned second domain comprises a fragment of at least 15 amino acids of SEQ ID NO: 2, SEQ ID NO: 3, SEQ ID NO: 4 or SEQ ID NO: 5, or a variant of the fragment having at least 75% homology with the fragment.

In an embodiment, the above-mentioned variant of a natriuretic peptide comprises an amino acid sequence having at least 75% homology with the amino acid sequence of SEQ ID NO: 2, SEQ ID NO: 3, SEQ ID NO: 4 or SEQ ID NO: 5.

In an embodiment, the above-mentioned second domain comprises the amino acid sequence of Formula II (SEQ ID NO: 58):

$$X^5\text{-}X^6\text{-}X^7\text{-}F\text{-}G\text{-}G\text{-}R\text{-}X^8\text{-}D\text{-}R\text{-}I\text{-}X^9 \quad (II)$$

wherein
$X^5$ is M, Nle, R-R-S-S, S-L-R-R-S-S, or is absent;
$X^6$ is C;
$X^7$ is H or is absent
$X^8$ is M or Nle;
$X^9$ is S-C-Y-R or G-A-Q-S-G-L-G-C-N-S-F-R-Y;
wherein
the C residue of $X^6$ forms a disulfide bridge with the C residue of $X^9$; and
when $X^5$ is Nle, said first domain is N-terminal to said second domain.

In an embodiment, the above-mentioned second domain comprises:
(i) M-C-H-F-G-G-R-M-D-R-I-S-C-Y-R, wherein the C residues at positions 2 and 13 form a disulfide bridge (SEQ ID NO: 22);
(ii) Nle-C-H-F-G-G-R-Nle-D-R-I-S-C-Y-R, wherein the C residues at positions 2 and 13 form a disulfide bridge (SEQ ID NO: 23);
(iii) C-F-G-G-R-M-D-R-I-G-A-Q-S-G-L-G-C-N-S-F-R-Y, wherein the C residues at positions 1 and 17 form a disulfide bridge (SEQ ID NO: 24);
(iv) C-F-G-G-R-Nle-D-R-I-G-A-Q-S-G-L-G-C-N-S-F-R-Y, wherein the C residues at positions 1 and 17 form a disulfide bridge (SEQ ID NO: 25);
(v) R-R-S-S-C-F-G-G-R-M-D-R-I-G-A-Q-S-G-L-G-C-N-S-F-R-Y, wherein the C residues at positions 5 and 21 form a disulfide bridge (SEQ ID NO: 26);
(vi) S-L-R-R-S-S-C-F-G-G-R-M-D-R-I-G-A-Q-S-G-L-G-C-N-S-F-R-Y, wherein the C residues at positions 7 and 23 form a disulfide bridge (SEQ ID NO: 59); or
(vii) M-C-F-G-G-R-M-D-R-I-G-A-Q-S-G-L-G-C-N-S-F-R-Y, wherein the C residues at positions 2 and 18 form a disulfide bridge (SEQ ID NO: 60).

In an embodiment, the above-mentioned second domain consists of:
(i) M-C-H-F-G-G-R-M-D-R-I-S-C-Y-R, wherein the C residues at positions 2 and 13 form a disulfide bridge (SEQ ID NO: 22);
(ii) Nle-C-H-F-G-G-R-Nle-D-R-I-S-C-Y-R, wherein the C residues at positions 2 and 13 form a disulfide bridge (SEQ ID NO: 23);
(iii) C-F-G-G-R-M-D-R-I-G-A-Q-S-G-L-G-C-N-S-F-R-Y, wherein the C residues at positions 1 and 17 form a disulfide bridge (SEQ ID NO: 24);
(iv) C-F-G-G-R-Nle-D-R-I-G-A-Q-S-G-L-G-C-N-S-F-R-Y, wherein the C residues at positions 1 and 17 form a disulfide bridge (SEQ ID NO: 25);
(v) R-R-S-S-C-F-G-G-R-M-D-R-I-G-A-Q-S-G-L-G-C-N-S-F-R-Y, wherein the C residues at positions 5 and 21 form a disulfide bridge (SEQ ID NO: 26);
(vi) S-L-R-R-S-S-C-F-G-G-R-M-D-R-I-G-A-Q-S-G-L-G-C-N-S-F-R-Y, wherein the C residues at positions 7 and 23 form a disulfide bridge (SEQ ID NO: 59); or
(vii) M-C-F-G-G-R-M-D-R-I-G-A-Q-S-G-L-G-C-N-S-F-R-Y, wherein the C residues at positions 2 and 18 form a disulfide bridge (SEQ ID NO: 60).

In an embodiment, the above-mentioned first domain is N-terminal to said second domain.

In an embodiment, the amino terminal of the above-mentioned bifunctional hormone is acetylated or acylated with a $C_3$-$C_{16}$ acyl group.

In an embodiment, the carboxy terminal residue of the above-mentioned bifunctional hormone is amidated.

In an embodiment, the above-mentioned first and second domains are covalently linked through a peptide bond.

In an embodiment, the above-mentioned bifunctional hormone comprises:
(i) H-f-R-W-G-K-P-M-C-H-F-G-G-R-M-D-R-I-S-C-Y-R, wherein the C residues at positions 9 and 20 form a disulfide bridge (SEQ ID NO: 61);
(ii) H-f-R-W-G-K-P-M-C-F-G-G-R-M-D-R-I-G-A-Q-S-G-L-G-C-N-S-F-R-Y, wherein the C residues at positions 9 and 25 form a disulfide bridge (SEQ ID NO: 62);
(iii) H-f-R-W-G-K-P-Nle-C-H-F-G-G-R-Nle-D-R-I-S-C-Y-R, wherein the C residues at positions 9 and 20 form a disulfide bridge (SEQ ID NO: 63);
(iv) H-f-R-W-G-K-P-Nle-C-F-G-G-R-Nle-D-R-I-G-A-Q-S-G-L-G-C-N-S-F-R-Y, wherein the C residues at positions 9 and 25 form a disulfide bridge (SEQ ID NO: 64);
(v) M-E-H-F-R-W-G-R-R-S-S-C-F-G-G-R-M-D-R-I-G-A-Q-S-G-L-G-C-N-S-F-R-Y, wherein the C residues at positions 12 and 28 form a disulfide bridge (SEQ ID NO: 65);
(vi) H-F-R-W-G-R-R-S-S-C-F-G-G-R-M-D-R-I-G-A-Q-S-G-L-G-C-N-S-F-R-Y, wherein the C residues at positions 10 and 26 form a disulfide bridge (SEQ ID NO: 66);
(vii) H-f-R-W-G-R-R-S-S-C-F-G-G-R-M-D-R-I-G-A-Q-S-G-L-G-C-N-S-F-R-Y, wherein the C residues at positions 10 and 26 form a disulfide bridge (SEQ ID NO: 67);
(viii) S-L-R-R-S-S-C-F-G-G-R-M-D-R-I-G-A-Q-S-G-L-G-C-N-S-F-R-Y-H-f-R-W, wherein the C residues at positions 7 and 23 form a disulfide bridge (SEQ ID NO: 68); or (ix) E-H-f-R-W-G-R-R-S-S-C-F-G-G-R-M-D-R-I-G-A-Q-S-G-L-G-C-N-S-F-R-Y, wherein the C residues at positions 11 and 27 form a disulfide bridge (SEQ ID NO: 69);
wherein f is D-phenylalanine.

In an embodiment, the above-mentioned bifunctional hormone consists of:
(i) Ac-H-f-R-W-G-K-P-M-C-H-F-G-G-R-M-D-R-I-S-C-Y-R-NH$_2$, wherein the C residues at positions 9 and 20 form a disulfide bridge (SEQ ID NO: 31);
(ii) Ac-H-f-R-W-G-K-P-M-C-F-G-G-R-M-D-R-I-G-A-Q-S-G-L-G-C-N-S-F-R-Y—NH$_2$, wherein the C residues at positions 9 and 25 form a disulfide bridge (SEQ ID NO: 33);
(iii) Ac-H-f-R-W-G-K-P-Nle-C-H-F-G-G-R-Nle-D-R-I-S-C-Y-R-NH$_2$, wherein the C residues at positions 9 and 20 form a disulfide bridge (SEQ ID NO: 34);
(iv) Ac-H-f-R-W-G-K-P-Nle-C-F-G-G-R-Nle-D-R-I-G-A-Q-S-G-L-G-C-N-S-F-R-Y-NH$_2$, wherein the C residues at positions 9 and 25 form a disulfide bridge (SEQ ID NO: 35);
(v) M-E-H-F-R-W-G-R-R-S-S-C-F-G-G-R-M-D-R-I-G-A-Q-S-G-L-G-C-N-S-F-R-Y-NH$_2$, wherein the C residues at positions 12 and 28 form a disulfide bridge (SEQ ID NO: 36);
(vi) Ac-H-F-R-W-G-R-R-S-S-C-F-G-G-R-M-D-R-I-G-A-Q-S-G-L-G-C-N-S-F-R-Y-NH$_2$, wherein the C residues at positions 10 and 26 form a disulfide bridge (SEQ ID NO: 38);
(vii) Ac-H-f-R-W-G-R-R-S-S-C-F-G-G-R-M-D-R-I-G-A-Q-S-G-L-G-C-N-S-F-R-Y-NH$_2$, wherein the C residues at positions 10 and 26 form a disulfide bridge (SEQ ID NO: 39);
(viii) S-L-R-R-S-S-C-F-G-G-R-M-D-R-I-G-A-Q-S-G-L-G-C-N-S-F-R-Y-H-f-R-W-NH$_2$, wherein the C residues at positions 7 and 23 form a disulfide bridge (SEQ ID NO: 40); or
(ix) Ac-E-H-f-R-W-G-R-R-S-S-C-F-G-G-R-M-D-R-I-G-A-Q-S-G-L-G-C-N-S-F-R-Y-NH$_2$, wherein the C residues at positions 11 and 27 form a disulfide bridge (SEQ ID NO: 42);
wherein
Ac represents an amino terminal acetylation;
NH$_2$ represents a carboxy terminal amidation; and
f is D-phenylalanine.

In another aspect, the present invention provides a composition comprising the above-mentioned bifunctional hormone, and a pharmaceutically acceptable carrier.

In another aspect, the present invention provides the above-mentioned bifunctional hormone for preventing and/or treating a renal disorder in a subject.

In another aspect, the present invention provides the above-mentioned bifunctional hormone for preventing and/or treating hypertension in a subject.

In another aspect, the present invention provides a pharmaceutical composition for preventing and/or treating a renal disorder in a subject comprising the above-mentioned bifunctional hormone, and a pharmaceutically acceptable carrier.

In another aspect, the present invention provides a pharmaceutical composition for preventing and/or treating hypertension in a subject comprising the above-mentioned bifunctional hormone, and a pharmaceutically acceptable carrier.

In another aspect, the present invention provides a method for preventing and/or treating a renal disorder in a subject comprising administering an effective amount of at least one of (a) the above-mentioned bifunctional hormone, or (b) the above-mentioned composition, to said subject.

In an embodiment, the above-mentioned administration is by intravenous infusion. In a further embodiment, the above-mentioned intravenous infusion is at a rate of about 1 ng/kg/min to about 10 µg/kg/min.

In another aspect, the present invention provides a method for preventing and/or treating hypertension in a subject comprising administering an effective amount of at least one of (a) the above-mentioned bifunctional hormone, or (b) the above-mentioned composition, to said subject.

In another aspect, the present invention provides a use of at least one of (a) the above-mentioned bifunctional hormone, or (b) the above-mentioned composition, for the preparation of a medicament for preventing and/or treating a renal disorder in a subject.

In another aspect, the present invention provides a use of at least one of (a) the above-mentioned bifunctional hormone, or (b) the above-mentioned composition, for preventing and/or treating a renal disorder in a subject.

In another aspect, the present invention provides a use of at least one of (a) the above-mentioned bifunctional hormone or (b) the above-mentioned composition, for preventing and/or treating hypertension in a subject.

In another aspect, the present invention provides a use of at least one of (a) the above-mentioned bifunctional hormone or (b) the above-mentioned composition, for the preparation of a medicament for preventing and/or treating hypertension in a subject.

In an embodiment, the above-mentioned renal disorder is acute kidney injury.

In another embodiment, the above-mentioned renal disorder is post-operative kidney injury or dysfunction.

In a further embodiment, the above-mentioned post-operative kidney injury or dysfunction results from cardiopulmonary bypass surgery for valve repair, aortic anurysm, organ transplantation, open heart surgery or coronary artery graft.

In an embodiment, the above-mentioned bifunctional hormone or composition is adapted for administration by intravenous infusion. In a further embodiment, the above-mentioned intravenous infusion is at a rate of about 1 ng/kg/min to about 10 µg/kg/min.

Other objects, advantages and features of the present invention will become more apparent upon reading of the following non-restrictive description of specific embodiments thereof, given by way of example only with reference to the accompanying drawings.

DISCLOSURE OF INVENTION

Figure 1:
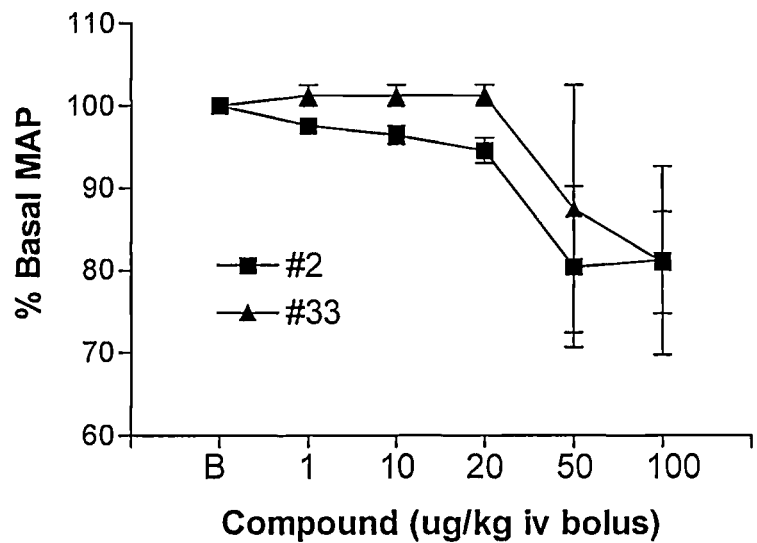
FIG. 1 shows (A) the effect on the blood pressure of incremental doses of peptides (SEQ ID NOs: 2 and 33) injected intravenously at bolus doses. The data were plotted as percent change from the baseline mean arterial pressure (MAP) (denoted by "B" in FIG. 1A). (B) the effect on the blood pressure of single doses (30 µg/kg/h infusion) of the peptides. MAP was recorded over an hour. The data are plotted as percent change from basal MAP as a function of time (min). #2=native ANP (SEQ ID NO:2), #33=bifunctional hormone of SEQ ID NO: 33.
Figure 1:
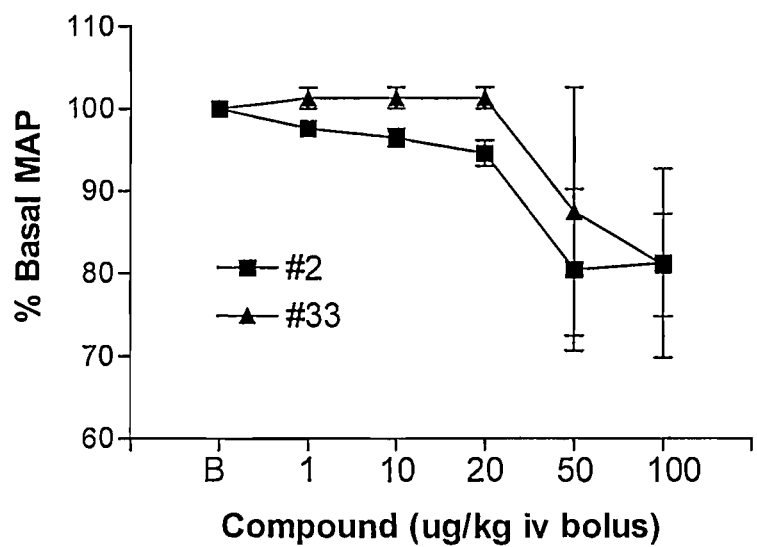

The present invention relates to a novel, bifunctional hormone, as well as to uses thereof, for example for the prevention and/or treatment of renal-related diseases or conditions, such as acute renal failure (ARF) or acute kidney injury (AKI). The bifunctional hormone exhibits a biological activity on an α-MSH (α-melanocyte-stimulating hormone) receptor and on at least one of the natriuretic peptide receptors.

Accordingly, in an aspect, the present invention provides a bifunctional hormone comprising:
(a) a first domain comprising an alpha-MSH peptide or a fragment, variant, or variant of a fragment thereof, said fragment, variant or variant of a fragment having alpha-MSH related hormonal activity; and
(b) a second domain covalently linked to said first domain, said second domain comprising a natriuretic peptide or a fragment, variant, or variant of a fragment thereof, said fragment, variant or variant of a fragment having natriuretic peptide related hormonal activity.

In an embodiment, wherein when the first domain is the alpha-MSH peptide of SEQ ID NO: 1; the second domain is the fragment, variant or variant of a fragment having natriuretic peptide related hormonal activity, and if the second domain is the natriuretic peptide of SEQ ID NOs: 2, 3, 4 or 5, the first domain is the fragment, variant or variant of a fragment having alpha-MSH related hormonal activity.

The present invention also provides a bifunctional hormone comprising a first domain having alpha-MSH-related biological activity covalently linked to a second domain having natriuretic peptide-related biological activity, wherein (i) said first domain is not the full-length (i.e. native) alpha-MSH peptide, (ii) said second domain is not a full-length (i.e. native) natriuretic peptide, or (iii) both (i) and (ii).

Melanocortins are pro-opiomelanocortin-derived mammalian peptide hormones that include adrenocorticotropic hormone (ACTH(1-39)), α-melanocyte-stimulating hormone ((α-MSH(1-13)), and related amino acid sequences including β- and γ-MSH. Melanocortin peptides have potent anti-infammatory/anticytokine activity (Lipton and Catania, *Immunol. Today* 18: 140-145, 1997). Melanocortins provides at least some of their activities via stimulation of the melanocortin receptors (MCRs). The melanocyte stimulating hormones (MSH) activity is partly ascribed by the binding and the activation of the melanocortin receptors of type 1 to 5 (MCR1-MCR5).

α-MSH binds with great affinity to type 1 receptor (MCR1), which is known to be expressed in several tissues and cells. β-MSH, γ-MSH and ACTH bind also to MCR1 but with lower affinity. MCR2 has been reported only to bind ACTH but none of the MSH peptides. γ-MSH binds with high affinity to MCR3 receptor and β-MSH binds with high affinity to MCR4 receptor.

α-MSH has been shown to inhibit major forms of inflammation processes (Lipton and Catania, *Immunol Today*, 18: 140-145, 1997) including:
1—Inhibition of neutrophils chemotactive acitvity (Catania, A. N. et al. *Peptides,* 17: 675-679, 1996);
2—Inhibition of cytokine (IL-1, TNF-α) release induced by LPS treatment;
3—Inhibition of TNF-α in response to bacterial endotoxin (Wong, K. Y. et al. *Neuroimmunomodulation,* 4: 37-41, 1997);
4—Inflammation reduction in experimental inflammatory bowel disease (Rajora, N. et al. *Peptides,* 18: 381-385, 1997);
5—Ischemia-Induced acute renal failure (Star, R. A. et al. *Proc. Natl. Acad. Sci. U.S.A,* 92: 8016-8020, 1995);
6—Increase of IL-8 release from dermal microvasculature endothelial cells (Hartmeyer, M. T., *J. Immunol,* 159: 1930-1937, 1997);

α-MSH effects are mediated by melanocortin receptors expressed in various cell types including macrophage, neutrophils, and renal tubules.

Natriuretic peptides are part of a family of peptides that are synthesized by three different genes (Flynn T G. *Pro. Soc. Exp. Biol. Med.* 213: 98-104, 1996; Levin E R et al. *N Eng J. Med* 339: 321-328, 1998; Ogawa Y et al. *Clin Exp Pharmacol physiol.* 22: 49-53, 1995; Rosenzweig A., *Annu Rev Biochem* 60: 229-255, 1991) and then stored as three different prohormones [i.e., 126 amino acid ANP, 108 amino acid brain natriuretic peptide (BNP), and 126-amino acid C-type natriuretic peptide (CNP) prohormones] (Levin E R et al. *N Eng J. Med* 339: 321-328, Vesely D L *Atrial Natriuretic Hormones.* Englewood Cliffs, N.J.: Prentice Hall, 1992, 1-256).

Within the 126-amino acid ANP prohormone are four peptide hormones, with blood pressure-lowering, natriuretic, diuretic, and/or kaliuretic properties in both animals and humans. These peptide hormones, numbered by their amino acid sequences beginning at the N-terminal end of the prohormone, are as follows:
residues 1-30 of the prohormone: long acting natriuretic peptide (LANP);
residues 31-67 of the prohormone: vessel dilator;
residues 79-98 of the prohormone: kaliuretic peptide; and
residues 99-126 of the prohormone: ANP.

The BNP and CNP genes, on the other hand, appear to each synthesize only one peptide hormone within their respective prohormones, i.e, BNP and CNP.

Atrial natriuretic peptide (ANP), a circulating hormone derived principally from cardiac atrial myocytes, plays a role in the control of salt and water homeostasis and blood pressure. In addition, ANP is a vasodilator and also has direct actions on the kidney including glomerular filtration increase, sodium reabsorption inhibition, and renal blood flow redistribution to promote natriuresis and diuresis.

Urodilatin is a kidney-derived member of the natriuretic peptide family and is formed from the same ANP prohormone and consists of the amino acid sequence 95-126. Except for the 4 amino acids at the N-terminus, it is identical to ANP (99-126). Urodilatin appears to be an important regulator of sodium and water handling in the kidney, as well as a mediator of sodium excretion in patients with congestive heart failure (CHF).

BNP produces similar biologic effects as ANP in healthy human. Infusion of BNP in normal men produced 2-fold increase in sodium excretion, 50% reduction in plasma renin, angiotensin II and aldosterone secretion. Cleavage of a 32 amino acid sequence from the C-terminal end of ProBNP results in human BNP (77-108) which is the physiologically active form in plasma.

CNP induces cardiovascular effects similar to the other natriuretic peptides. The terminal amino acid sequence 105-126 is cleaved from proCNP to yield a biologically active form of CNP.

Most biological effects of ANP and BNP are mediated by guanylate cyclase coupled cell surface receptor, the A-receptor (NPR-A) (Garbers, D L, *Cell* 1992, 71: 1-4). CNP is a specific ligand for the B-receptor (NPR-B), another guanylate cyclase coupled NP receptor (Maack T, *Ann. Rev. physiol.* 1992, 54: 11-27). The third receptor, the so-called NP clearance receptor (NPR-C), binds ANP, BNP and CNP. Apart from a major role in the clearance of NP in the whole body (Maack T, *Ann. Rev. physiol.* 1992, 54: 11-27), it has also been reported that several effects of ANP are mediated via NPR-C receptor (Maack T, *Kidney Int* 1996, 49: 1732-1737). Apart from binding to the NP receptors, natriuretic peptides are also cleared through proteolysis by neutral endopeptidases. All three subtypes of natriuretic peptide receptors (NPR-A, NPR-B and NPR-C) have been demonstrated to be expressed in diverse tissues including the renal system and the heart (Nunez, D J R et al., *J. Clin Invest.* 1992, 90: 1966-1971).

The native amino acid sequence of α-MSH, ANP, urodilatin, BNP and CNP are given in Table 1 below.

TABLE I

| Name | SEQ ID NOs: | Amino acid sequences |
|---|---|---|
| α-MSH | 1 | Ac-S-Y-S-M-E-H-F-R-W-G-K-P-V |
| ANP | 2 | S-L-R-R-S-S-[C-F-G-G-R-M-D-R-I-G-A-Q-S-G-L-G-C]-N-S-F-R-Y |
| Urodilatin | 3 | T-A-P-R-S-L-R-R-S-S-[C-F-G-G-R-M-D-R-I-G-A-Q-S-G-L-G-C]-N-S-F-R-Y |
| BNP | 4 | S-P-K-M-V-Q-G-S-G-[C-P-G-R-K-M-D-R-I-S-S-S-S-G-L-G-C]-K-V-L-R-R-H |
| CNP | 5 | G-L-S-K-G-[C-F-G-L-K-L-D-R-I-G-S-M-S-G-L-G-C] |

[ ] = cyclized peptide via a disulfide bridge; the amino acid to the right of "[" forms a bridge with the amino acid to the left of "]".

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc. Other amino acids include for example norleucine, norvaline, cyclohexyl alanine, biphenyl alanine, homophenyl alanine, naphthyl alanine, pyridyl alanine, phenyl alanines substituted at the ortho, para and meta positions with alkoxy, halogen or nitro groups etc. These amino acids are well known in the art of biochemistry/peptide chemistry.

"Biological activity" or "bioactivity" or "activity" or "biological function", which are used interchangeably herein, refers to a function that is directly or indirectly performed by a peptide hormone or a bifunctional hormone, or by any fragment thereof. Biological activities include, for example, binding to a hormone receptor, and eliciting hormone response/activity.

Alpha-MSH-related biological activity generally refers to a biological (e.g., hormonal) activity of the native alpha-MSH, such as anti-inflammatory and/or anti-cytokine activity. Natriuretic peptide-related biological activity generally refers to one of the hormonal activities of native ANP, native BNP, native CNP or native urodilatin, such as blood pressure-lowering, natriuretic, diuretic, vasodilator and/or kaliuretic activity. Determination of an alpha-MSH-related biological activity (e.g., an alpha-MSH receptor binding activity) may be performed for example by an in vitro assay using MCR1 receptor expressing cells, as described in Example 2. Determination of a natriuretic peptide related biological activity (e.g., a natriuretic peptide receptor binding activity) may be performed by an in vitro assay using ANP receptor expressing cells, as described in Example 2.

As used herein, the term "fragment" refers to a portion/segment of a peptide which retains the activity of the peptide (e.g., an alpha-MSH peptide or natriuretic peptide related hormonal activity). The term variant refers to a domain having at least one modification as compared to a wild-type peptide (e.g., an alpha-MSH peptide and/or a natriuretic peptide) or to a fragment thereof.

In embodiments, the modification is a deletion, an insertion, a substitution or a chemical modification of one or more amino acids. The modification may be, for example, a deletion of (e.g., one to ten) consecutive or non-consecutive amino acids, a substitution of (e.g., one to ten) amino acids, one or more substitution(s) of a naturally occurring amino acid (L-amino acid) by a corresponding D-amino acid, an extension of the sequence by e.g., one, two, three or more amino acids.

In an embodiment, the above-mentioned substitution(s) are conserved amino acid substitutions.

As used herein, the term "conserved amino acid substitutions" (or sometimes "conservative amino acid substitutions") refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In other embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In other embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine(sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylix acid, beta-2-thienylalanine, methionine sulfoxide, homoarginine, N-acetyl lysine, 2-amino butyric acid, 2-amino butyric acid, 2,4, -diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In other embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Biol.* 179: 125-142, 1984). Genetically encoded hydrophobic amino acids include Gly, Ala, Phe, Val, Leu, Ile, Pro, Met and Trp, and genetically, encoded hydrophilic amino acids include Thr, His, Glu, Gln, Asp, Arg, Ser, and Lys.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid.

In addition to the substitutions outlined above, synthetic amino acids providing similar side chain functionality can also be introduced into the peptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g., —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties, (e.g., (—C=O)—$CH_2$—), (—CHOH)—$CH_2$—), ($CH_2$—$CH_2$—), (—C=S)—NH—), or (—NH—C=O) for (—C=O)—NH—)).

Other modifications are also included within the definition of variant of the bifunctional hormone of the present invention. For example, the size of the peptides can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, ketomethylene pseudopeptides, β-turn dipeptide cores and β-aminoalcohols for these purposes are known to peptide chemists and are described in for example *Peptidomimetic protocols* (Methods in molecular medicine Vol. 23) W. M. Kazmierski (ed.), Humana Press and *Advances in Amino Acid Mimetics and Peptidomimetics*, Vols. 1 & 2, A. Abell (Ed).

Covalent modifications of the peptide are thus included within the scope of the present invention. Such modifications may be introduced into the bifunctional hormone for example by reacting targeted amino acid residues of the polypeptide with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters, e.g. methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N=C=N-R') such as 1-cyclohexyl-3-(2-morpholinyl-(4-ethyl)carbodiimide or 1-ethyl-3-(4-azonia-4,4-dimethylpentyl)carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (e.g., $C_6$-$C_{18}$) to the peptides may confer additional biological properties such as protease resistance, plasma protein binding, increased plasma half-life, intracellular penetration, etc. The above description of modification of a bifunctional hormone does not limit the scope of the approaches nor the possible modifications that can be engineered.

In embodiments, the first domain of the bifunctional hormone may be covalently linked to the second domain either directly (e.g., through a peptide bond) or via a suitable linker moiety, e.g., a linker of one or more amino acids (e.g., a polyglycine linker) or another type of chemical linker (e.g., a carbohydrate linker, a lipid linker, a fatty acid linker, a polyether linker, PEG, etc. (see, e.g., Hermanson (1996) Bioconjugate techniques). In an embodiment, one or more additional domain(s) (e.g., a domain having a biological activity) may be inserted between the first and second domains. In an embodiment, the first and second domain are covalently linked through a peptide bond.

In an embodiment, the first domain comprises at least one modification as compared to the naturally occurring sequence of alpha-MSH (SEQ ID NO: 1).

In an embodiment, the above-mentioned first domain comprises a fragment of at least 4 amino acids of the peptide of SEQ ID NO: 1, or a variant of the fragment having at least 75% homology with the fragment.

In another embodiment, the above-mentioned variant of an alpha-MSH peptide comprises an amino acid sequence having at least 75% homology with the amino acid sequence of SEQ ID NO: 1.

"Homology" and "homologous" refers to sequence similarity between two polypeptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid or amino acid sequence is "homologous" to another sequence if the two sequences are substantially identical and the functional activity of the sequences is conserved (as used herein, the term 'homologous' does not infer evolutionary relatedness). Two nucleic acid or amino acid sequences are considered "substantially identical" if, when optimally aligned (with gaps permitted), they share at least about 75% sequence similarity or identity, or if the sequences share defined functional motifs. In alternative embodiments, sequence similarity in optimally aligned substantially identical sequences may be at least 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with a sequence described herein.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215: 403-10 (using the published default settings). Software for performing BLAST analysis may be available through the National Center for Biotechnology Information web site (http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

Substantially complementary nucleic acids are nucleic acids in which the complement of one molecule is substantially identical to the other molecule. An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

In an embodiment, the above-mentioned first domain comprises the amino acid sequence of Formula I (SEQ ID NO: 47):

$$X^2-H-X^1-R-W-X^3 \quad (I)$$

wherein:

$X^1$ is L-Phe or D-Phe;

$X^2$ is E, M-E or is absent;

$X^3$ is G-K-P-$X^4$, G-K-P, G-K, G or is absent;

$X^4$ is M, V or Nle

In a further embodiment, the above-mentioned first domain comprises:

| (i)   | H-X¹-R-W-G-K-P-X⁴; | (SEQ ID NO: 48) |
|-------|--------------------|-----------------|
| (ii)  | M-E-H-X¹-R-W-G;    | (SEQ ID NO: 17) |
| (iii) | H-X¹-R-W-G;        | (SEQ ID NO: 49) |
| (iv)  | E-H-X¹-R-W-G;      | (SEQ ID NO: 50) |
| or    |                    |                 |
| (v)   | H-X¹-R-W;          | (SEQ ID NO: 20) | wherein $X^1$ is L-Phe or D-Phe, and $X^4$ is M, V or Nle.

In an embodiment, the above-mentioned first domain contains 10 amino acids or less. In another embodiment, the above-mentioned first domain contains 9 amino acids or less. In another embodiment, the above-mentioned first domain contains 8 amino acids or less. In another embodiment, the above-mentioned first domain contains 7 amino acids or less. In another embodiment, the above-mentioned first domain contains 6 amino acids or less. In another embodiment, the above-mentioned first domain contains 5 amino acids or less.

In an embodiment, the above-mentioned first domain consists of:

| (i)    | H-f-R-W-G-K-P-V;   | (SEQ ID NO: 51) |
|--------|--------------------|-----------------|
| (ii)   | H-f-R-W-G-K-P-M;   | (SEQ ID NO: 52) |
| (iii)  | H-f-R-W-G-K-P-Nle; | (SEQ ID NO: 53) |
| (iv)   | H-f-R-W-G-K-P;     | (SEQ ID NO: 54) |
| (v)    | M-E-H-F-R-W-G;     | (SEQ ID NO: 11) |
| (vi)   | H-f-R-W-G;         | (SEQ ID NO: 55) |
| (vii)  | E-H-F-R-W;         | (SEQ ID NO: 56) |
| (ix)   | E-H-f-R-W-G;       | (SEQ ID NO: 57) |
| or     |                    |                 |
| (iv)   | H-f-R-W;           | (SEQ ID NO: 6)  | wherein f is D-phenylalanine.

In an embodiment, if the first domain is located at the N-terminal portion of the bifunctional hormone, the amino-terminal residue is acylated with a $C_2$-$C_{16}$ acyl group. In a further embodiment, the amino-terminal residue is acetylated.

Representative examples of amino acid sequences of the first domain of the bifunctional hormone according to the present invention are listed in Table I.

TABLE I

| SEQ ID NOs: | Amino acid sequence |
| --- | --- |
| 6 | H-f-R-W |
| 7 | Ac-H-f-R-W-G-K-P-M |
| 8 | Ac-H-f-R-W |
| 9 | Ac-H-f-R-W-G |
| 10 | M-E-H-f-R-W-G |
| 11 | M-E-H-F-R-W-G |
| 12 | Ac-H-f-R-W-G-K-P-Nle |
| 13 | Ac-H-F-R-W-G |
| 14 | Ac-E-H-F-R-W-G |
| 15 | Ac-E-H-f-R-W-G |
| 16 | Ac-H-Xa-R-W-G-K-P-Xb |
| 17 | M-E-H-Xa-R-W-G |
| 18 | Ac-H-Xa-R-W-G |
| 19 | Ac-E-H-Xa-R-W |
| 20 | H-Xa-R-W |
| 21 | Ac-H-Xa-R-W | f is D-Phe
Xa is L-Phe or D-Phe and
Xb is Met, Val or Nle

In an embodiment, the second domain of the bifunctional hormone of the present invention comprises at least one modification as compared to the naturally occurring sequence of ANP (SEQ ID NO: 2), urodilatin (SEQ ID NO: 3), BNP (SEQ ID NO: 4) or CNP (SEQ ID NO: 5).

In an embodiment, the second domain comprises a fragment of at least 15 amino acids of SEQ ID NO: 2, SEQ ID NO: 3, SEQ ID NO: 4 or SEQ ID NO: 5, or a variant of the fragment having at least 75% homology with the fragment.

In an embodiment, the above-mentioned variant of a natriuretic peptide comprises an amino acid sequence having at least 75% homology with the amino acid sequence of SEQ ID NO: 2, SEQ ID NO: 3, SEQ ID NO: 4 or SEQ ID NO: 5.

In an embodiment, the second domain comprises the amino acid sequence of Formula III (SEQ ID NO: 72):

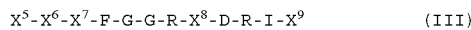

$$X^5-X^6-X^7-F-G-G-R-X^8-D-R-I-X^9 \qquad (III)$$

wherein
$X^5$ is M, Nle, R-R-S-S, S-L-R-R-S-S, or is absent;
$X^6$ is E, D, or C;
$X^7$ is H or is absent
$X^8$ is M or Nle;
$X^9$ is S-K-Y-R, S-C-Y-R or G-A-Q-S-G-L-G-C-N-S-F-R-Y;
wherein
when $X^6$ is C and $X^9$ is S-C-Y-R or G-A-Q-S-G-L-G-C-N-S-F-R-Y, and the C residue of $X^6$ forms a disulfide bridge with the C residue of $X^9$;
when $X^6$ is E or D, $X^9$ is S-K-Y-R, and the K residue of $X^9$ forms a lactam bridge with the E or D residue of $X^6$.

In an embodiment, the second domain comprises the amino acid sequence of Formula II (SEQ ID NO: 58):

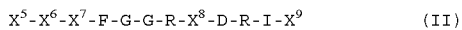

$$X^5-X^6-X^7-F-G-G-R-X^8-D-R-I-X^9 \qquad (II)$$

wherein
$X^5$ is M, Nle, R-R-S-S, S-L-R-R-S-S, or is absent;
$X^6$ is C;
$X^7$ is H or is absent
$X^8$ is M or Nle;
$X^9$ is S-C-Y-R or G-A-Q-S-G-L-G-C-N-S-F-R-Y;
wherein
the C residue of $X^6$ forms a disulfide bridge with the C residue of $X^9$; and
when $X^5$ is Nle, said first domain is N-terminal to said second domain.

In an embodiment, the second domain comprises the amino acid sequence of Formula III (SEQ ID NO: 71):

$$X^5-X^6-X^7-F-G-G-R-X^8-D-R-I-X^9 \qquad (III)$$

wherein
$X^5$ is M, Nle, R-R-S-S, S-L-R-R-S-S, or is absent;
$X^6$ is E or D;
$X^7$ is H or is absent;
$X^8$ is M or Nle;
$X^9$ is S-K-Y-R;
wherein
the K residue of $X^9$ forms a lactam bridge with the E or D residue of $X^6$.

In an embodiment, the above-mentioned second domain contains 25 amino acids or less. In another embodiment, the above-mentioned second domain contains 24 amino acids or less. In another embodiment, the above-mentioned second domain contains 23 amino acids or less. In another embodiment, the above-mentioned second domain contains 22 amino acids or less. In another embodiment, the above-mentioned second domain contains 21 amino acids or less. In another embodiment, the above-mentioned second domain contains 20 amino acids or less. In another embodiment, the above-mentioned second domain contains 19 amino acids or less. In another embodiment, the above-mentioned second domain contains 18 amino acids or less. In another embodiment, the above-mentioned second domain contains 17 amino acids or less. In another embodiment, the above-mentioned second domain contains 16 amino acids or less.

In an embodiment, the second domain comprises:
(i) M-C-H-F-G-G-R-M-D-R-I-S-C-Y-R, wherein the C residues at positions 2 and 13 form a disulfide bridge (SEQ ID NO: 22);
(ii) Nle-C-H-F-G-G-R-Nle-D-R-I-S-C-Y-R, wherein the C residues at positions 2 and 13 form a disulfide bridge (SEQ ID NO: 23);
(iii) C-F-G-G-R-M-D-R-I-G-A-Q-S-G-L-G-C-N-S-F-R-Y, wherein the C residues at positions 1 and 17 form a disulfide bridge (SEQ ID NO: 24);
(iv) C-F-G-G-R-Nle-D-R-I-G-A-Q-S-G-L-G-C-N-S-F-R-Y, wherein the C residues at positions 1 and 17 form a disulfide bridge (SEQ ID NO: 25);
(v) R-R-S-S-C-F-G-G-R-M-D-R-I-G-A-Q-S-G-L-G-C-N-S-F-R-Y, wherein the C residues at positions 5 and 21 form a disulfide bridge (SEQ ID NO: 26);
(vi) Nle-E-H-F-G-G-R-Nle-D-R-I-S-K-Y-R, wherein the E residue at position 2 and the K residue at position 13 form a lactam bridge (SEQ ID NO: 70);

(vii) S-L-R-R-S-S-C-F-G-G-R-M-D-R-I-G-A-Q-S-G-L-G-C-N-S-F-R-Y, wherein the C residues at positions 7 and 23 form a disulfide bridge (SEQ ID NO: 59); or (viii) M-C-F-G-G-R-M-D-R-I-G-A-Q-S-G-L-G-C-N-S-F-R-Y, wherein the C residues at positions 2 and 18 form a disulfide bridge (SEQ ID NO: 60).

In an embodiment, the second domain consists of:

(i) M-C-H-F-G-G-R-M-D-R-I-S-C-Y-R, wherein the C residues at positions 2 and 13 form a disulfide bridge (SEQ ID NO: 22);

(ii) Nle-C-H-F-G-G-R-Nle-D-R-I-S-C-Y-R, wherein the C residues at positions 2 and 13 form a disulfide bridge (SEQ ID NO: 23);

(iii) C-F-G-G-R-M-D-R-I-G-A-Q-S-G-L-G-C-N-S-F-R-Y, wherein the C residues at positions 1 and 17 form a disulfide bridge (SEQ ID NO: 24);

(iv) C-F-G-G-R-Nle-D-R-I-G-A-Q-S-G-L-G-C-N-S-F-R-Y, wherein the C residues at positions 1 and 17 form a disulfide bridge (SEQ ID NO: 25);

(v) R-R-S-S-C-F-G-G-R-M-D-R-I-G-A-Q-S-G-L-G-C-N-S-F-R-Y, wherein the C residues at positions 5 and 21 form a disulfide bridge (SEQ ID NO: 26);

(vi) Nle-E-H-F-G-G-R-Nle-D-R-I-S-K-Y-R, wherein the E residue at position 2 and the K residue at position 13 form a lactam bridge (SEQ ID NO: 70);

(vii) S-L-R-R-S-S-C-F-G-G-R-M-D-R-I-G-A-Q-S-G-L-G-C-N-S-F-R-Y, wherein the C residues at positions 7 and 23 form a disulfide bridge (SEQ ID NO: 59); or (viii) M-C-F-G-G-R-M-D-R-I-G-A-Q-S-G-L-G-C-N-S-F-R-Y, wherein the C residues at positions 2 and 18 form a disulfide bridge (SEQ ID NO: 60).

Representative examples of amino acid sequences of the second domain of the bifunctional hormone according to the present invention are listed below in Table II.

TABLE II

| SEQ ID NOs: | Amino acid sequence |
|---|---|
| 22 | M-[C-H-F-G-G-R-M-D-R-I-S-C]-Y-R |
| 23 | Nle-[C-H-F-G-G-R-Nle-D-R-I-S-C]-Y-R |
| 24 | [C-F-G-G-R-M-D-R-I-G-A-Q-S-G-L-G-C]-N-S-F-R-Y |
| 25 | [C-F-G-G-R-Nle-D-R-I-G-A-Q-S-G-L-G-C]-N-S-F-R-Y |
| 26 | R-R-S-S-[C-F-G-G-R-M-D-R-I-G-A-Q-S-G-L-G-C]-N-S-F-R-Y |
| 27 | S-P-K-M-V-Q-G-S-G-[C-P-G-R-K-M-D-R-I-S-S-S-S-G-L-G-C]-K-V-L-R-R-H |
| 28 | P-K-P-V-Q-G-S-G-[C-P-G-R-K-M-D-R-I-S-S-S-S-G-L-G-C]-K-V-L-R-R-H |

[ ] = cyclized peptide via a disulfide bridge; the amino acid to the right of "[" forms a bridge with the amino acid to the left of "]".

In embodiments, the first and second domains may be linked C-terminus to N-terminus, C-terminus to C-terminus, N-terminus to N-terminus, or N-terminus to C-terminus. In an embodiment, each of the first domain (alpha-MSH peptide) and the second domain (natriuretic peptide) has an N-terminal amino acid and a C-terminal amino acid, and the C-terminal amino acid of the first domain is covalently linked to the N-terminal amino acid of the second domain. In an embodiment, the first domain is N-terminal to the second domain.

In embodiments, the N— and/or C-terminal amino acids may be modified by amidation, acetylation, acylation or other modifications known in the art. In an embodiment, the amino terminal residue (i.e., the free amino group at the N-terminal end of the peptide) of the bifunctional hormone is modified (e.g., for protection against degradation). In an embodiment, the modification is acylation with a $C_2$-$C_{16}$ acyl group, in a further embodiment, the modification is acetylation.

In an embodiment, the carboxy terminal residue (i.e., the free carboxy group at the C-terminal end of the peptide) of said bifunctional hormone is modified (e.g., for protection against degradation). In an embodiment, the modification is an amidation.

In an embodiment, the above-mentioned bifunctional hormone contains about 100 amino acids or less. In a further embodiment, the above-mentioned bifunctional hormone contains about 90 amino acids or less. In a further embodiment, the above-mentioned bifunctional hormone contains about 80 amino acids or less. In a further embodiment, the above-mentioned bifunctional hormone contains about 70 amino acids or less. In a further embodiment, the above-mentioned bifunctional hormone contains about 60 amino acids or less. In a further embodiment, the above-mentioned bifunctional hormone contains about 50 amino acids or less. In a further embodiment, the above-mentioned bifunctional hormone contains about 40 amino acids or less. In a further embodiment, the above-mentioned bifunctional hormone contains about 30 amino acids or less. In a further embodiment, the above-mentioned bifunctional hormone contains between about 20 to about 30 amino acids.

In an embodiment, the bifunctional hormone comprises:

(i) H-f-R-W-G-K-P-M-C-H-F-G-G-R-M-D-R-I-S-C-Y-R wherein the C residues at positions 9 and 20 form a disulfide bridge (SEQ ID NO: 61);

(ii) H-f-R-W-G-K-P-M-C-F-G-G-R-M-D-R-I-G-A-Q-S-G-L-G-C-N-S-F-R-Y, wherein the C residues at positions 9 and 25 form a disulfide bridge (SEQ ID NO: 62);

(iii) H-f-R-W-G-K-P-Nle-C-H-F-G-G-R-Nle-D-R-I-S-C-Y-R, wherein the C residues at positions 9 and 20 form a disulfide bridge (SEQ ID NO: 63);

(iv) H-f-R-W-G-K-P-Nle-C-F-G-G-R-Nle-D-R-I-G-A-Q-S-G-L-G-C-N-S-F-R-Y, wherein the C residues at positions 9 and 25 form a disulfide bridge (SEQ ID NO: 64);

(v) M-E-H-F-R-W-G-R-R-S-S-C-F-G-G-R-M-D-R-I-G-A-Q-S-G-L-G-C-N-S-F-R-Y, wherein the C residues at positions 12 and 28 form a disulfide bridge (SEQ ID NO: 65);

(vi) H-F-R-W-G-R-R-S-S-C-F-G-G-R-M-D-R-I-G-A-Q-S-G-L-G-C-N-S-F-R-Y, wherein the C residues at positions 10 and 26 form a disulfide bridge (SEQ ID NO: 66);

(vii) H-f-R-W-G-R-R-S-S-C-F-G-G-R-M-D-R-I-G-A-Q-S-G-L-G-C-N-S-F-R-Y, wherein the C residues at positions 10 and 26 form a disulfide bridge (SEQ ID NO: 67);

(viii) S-L-R-R-S-S-C-F-G-G-R-M-D-R-I-G-A-Q-S-G-L-G-C-N-S-F-R-Y-H-f-R-W, wherein the C residues at positions 7 and 23 form a disulfide bridge (SEQ ID NO: 68); or (ix) E-H-f-R-W-G-R-R-S-S-C-F-G-G-R-M-D-R-I-G-A-Q-S-G-L-G-C-N-S-F-R-Y, wherein the C residues at positions 11 and 27 form a disulfide bridge (SEQ ID NO: 69);

wherein f is D-phenylalanine.

In an embodiment, the bifunctional hormone consists of:

(i) Ac-H-f-R-W-G-K-P-M-C-H-F-G-G-R-M-D-R-I-S-C-Y-R-NH$_2$, wherein the C residues at positions 9 and 20 form a disulfide bridge (SEQ ID NO: 31);

(ii) Ac-H-f-R-W-G-K-P-M-C-F-G-G-R-M-D-R-I-G-A-Q-S-G-L-G-C-N-S-F-R-Y-NH$_2$, wherein the C residues at positions 9 and 25 form a disulfide bridge (SEQ ID NO: 33);

(iii) Ac-H-f-R-W-G-K-P-Nle-C-H-F-G-G-R-Nle-D-R-I-S-C-Y-R-NH$_2$, wherein the C residues at positions 9 and 20 form a disulfide bridge (SEQ ID NO: 34);

(iv) Ac-H-f-R-W-G-K-P-Nle-C-F-G-G-R-Nle-D-R-I-G-A-Q-S-G-L-G-C-N-S-F-R-Y-NH$_2$, wherein the C residues at positions 9 and 25 form a disulfide bridge (SEQ ID NO: 35);

(v) M-E-H-F-R-W-G-R-R-S-S-C-F-G-G-R-M-D-R-I-G-A-Q-S-G-L-G-C-N-S-F-R-Y-NH$_2$, wherein the C residues at positions 12 and 28 form a disulfide bridge (SEQ ID NO: 36);

(vi) Ac-H-F-R-W-G-R-R-S-S-C-F-G-G-R-M-D-R-I-G-A-Q-S-G-L-G-C-N-S-F-R-Y-NH$_2$, wherein the C residues at positions 10 and 26 form a disulfide bridge (SEQ ID NO: 38);

(vii) Ac-H-f-R-W-G-R-R-S-S-C-F-G-G-R-M-D-R-I-G-A-Q-S-G-L-G-C-N-S-F-R-Y-NH$_2$, wherein the C residues at positions 10 and 26 form a disulfide bridge (SEQ ID NO: 39);

(viii) S-L-R-R-S-S-C-F-G-G-R-M-D-R-I-G-A-Q-S-G-L-G-C-N-S-F-R-Y-H-f-R-W-NH$_2$, wherein the C residues at positions 7 and 23 form a disulfide bridge (SEQ ID NO: 40); or (ix) Ac-E-H-f-R-W-G-R-R-S-S-C-F-G-G-R-M-D-R-I-G-A-Q-S-G-L-G-C-N-S-F-R-Y-NH$_2$, wherein the C residues at positions 11 and 27 form a disulfide bridge (SEQ ID NO: 42);

wherein

Ac represents an amino terminal acetylation;

NH$_2$ represents a carboxy terminal amidation; and f is D-phenylalanine.

The present invention further includes pharmaceutically acceptable salts of the above-mentioned bifunctional hormone.

The bifunctional hormone of the invention may be produced by expression in a host cell comprising a nucleic acid encoding the bifunctional hormone (recombinant expression) or by chemical synthesis (e.g., solid-phase peptide synthesis). Peptides can be readily synthesized by automated solid phase procedures well known in the art. Suitable syntheses can be performed by utilizing "T-boc" or "Fmoc" procedures. Techniques and procedures for solid phase synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985. Commercial providers of peptide synthetic services may also be used to prepare synthetic peptides in the the D- or L-configuration. Such providers include, for example, Advanced ChemTech (Louisville, Ky.), Applied Biosystems (Foster City, Calif.), Anaspec (San Jose, Calif.), and Cell Essentials (Boston, Mass.).

Peptides and peptide analogues comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation, cyclization/formation of a loop within the peptide [e.g., via formation of a disulphide bridge between Cys residues]) using methods well known in the art. Therefore, in embodiments, in cases where a bifunctional hormone described herein contains naturally occurring amino acids encoded by the genetic code, the bifunctional hormone may be produced using recombinant methods, and may in embodiments be subjected to for example the just-noted modifications (e.g., acylation, amidation, cyclization). Accordingly, in another aspect, the invention further provides a nucleic acid encoding the above-mentioned bifunctional hormone. The invention also provides a vector comprising the above-mentioned nucleic acid. In yet another aspect, the present invention provides a cell (e.g., a host cell) comprising the above-mentioned nucleic acid and/or vector. The invention further provides a recombinant expression system, vectors and host cells, such as those described above, for the expression/production of a peptide or bifunctional hormone of the invention, using for example culture media, production, isolation and purification methods well known in the art.

Such vectors comprise a nucleic acid sequence capable of encoding such a peptide operably linked to one or more transcriptional regulatory sequence(s). In an embodiment, the peptide is a fusion peptide containing a domain which facilitates its purification (e.g., His-tag, GST-tag). Nucleic acids may be introduced into cells for expression using standard recombinant techniques for stable or transient expression. Nucleic acid molecules of the invention may include any chain of two or more nucleotides including naturally occurring or non-naturally occurring nucleotides or nucleotide analogues.

"Recombinant expression" refers to the production of a peptide or polypeptide (e.g., a binfunctional hormone) by recombinant techniques, wherein generally, a nucleic acid encoding peptide or polypeptide is inserted into a suitable expression vector which is in turn used to transform/transfect a host cell to produce the protein. The term "recombinant" when made in reference to a protein or a polypeptide refers to a peptide, polypeptide or protein molecule which is expressed using a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e., by human intervention. Recombinant nucleic acid constructs may for example be introduced into a host cell by transformation/transfection. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors".

A recombinant expression vector of the present invention can be constructed by standard techniques known to one of ordinary skill in the art and found, for example, in Sambrook et al. (1989) in *Molecular Cloning: A Laboratory Manual*. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (*Molecular Cloning: A Laboratory Manual*, 2$^{nd}$ Edition, Cold Spring Harbor Laboratory press (1989)), and other laboratory manuals. Methods for introducing DNA into mammalian cells in vivo are also known, and may be used to deliver the vector DNA of the invention to a subject for gene therapy.

"Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

As used herein, the term "transfection" or "transformation" generally refers to the introduction of a nucleic acid, e.g., via an expression vector, into a recipient cell by nucleic acid-mediated gene transfer.

A cell (e.g., a host cell or indicator cell), tissue, organ, or organism into which has been introduced a foreign nucleic acid (e.g., exogenous or heterologous DNA [e.g. a DNA construct]), is considered "transformed", "transfected", or "transgenic". A transgenic or transformed cell or organism also includes progeny of the cell or organism and progeny produced from a breeding program employing a transgenic organism as a parent and exhibiting an altered phenotype resulting from the presence of a recombinant nucleic acid construct. A transgenic organism is therefore an organism that has been transformed with a heterologous nucleic acid, or the progeny of such an organism that includes the transgene. The introduced DNA may be integrated into chromosomal DNA of the cell's genome, or alternatively may be maintained episomally (e.g., on a plasmid). Methods of transfection are well known in the art (see for example, Sambrook et al., 1989, supra; Ausubel et al., 1994 supra).

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. As used herein, the term "selectable marker" is used broadly to refer to markers which confer an identifiable trait to the indicator cell. Non-limiting example of selectable markers include markers affecting viability, metabolism, proliferation, morphology and the like. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

The peptides of the invention can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may for example be used.

In an embodiment, the above-mentioned bifunctional hormone is substantially pure. A compound is "substantially pure" when it is separated from the components that naturally accompany it. Typically, a compound is substantially pure when it is at least 60%, more generally 75%, preferably over 90% and more preferably over 95%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

In another aspect, the present invention also provides a pharmaceutical composition comprising the above-described bifunctional hormone and a pharmaceutically acceptable carrier or excipient.

In another aspect, the present invention also provides a pharmaceutical composition for preventing and/or treating a renal disorder in a subject comprising the above-described bifunctional hormone and a pharmaceutically acceptable carrier or excipient.

In another aspect, the present invention also provides a pharmaceutical composition for preventing and/or treating hypertension in a subject comprising the above-described bifunctional hormone and a pharmaceutically acceptable carrier or excipient.

The present invention further provides a method for preventing and/or treating a renal disorder in a subject comprising administering an effective amount of at least one of (a) the above-mentioned bifunctional hormone, or (b) the above-mentioned pharmaceutical composition, to said subject.

In another aspect, the present invention also provides a method for preventing and/or treating hypertension in a subject comprising administering an effective amount of at least one of (a) the above-mentioned bifunctional hormone, or (b) the above-mentioned pharmaceutical composition, to said subject.

The invention further relates to a use of the above-described bifunctional hormone for the preparation of a medicament.

In another aspect, the present invention provides a use of at least one of (a) the above-mentioned bifunctional hormone, or (b) the above-mentioned pharmaceutical composition, for the preparation of a medicament for preventing and/or treating a renal disorder in a subject.

In another aspect, the present invention provides a use of at least one of (a) the above-mentioned bifunctional hormone, or (b) the above-mentioned pharmaceutical composition, for preventing and/or treating a renal disorder in a subject.

In another aspect, the present invention provides a use of at least one of (a) the above-mentioned bifunctional hormone, or (b) the above-mentioned pharmaceutical composition, for the preparation of a medicament for preventing and/or treating hypertension in a subject.

In another aspect, the present invention provides a use of at least one of (a) the above-mentioned bifunctional hormone, or (b) the above-mentioned pharmaceutical composition, for preventing and/or treating hypertension in a subject.

An "effective amount" refers to an amount effective, at dosages and for periods of time necessary, to achieve the desired prophylactic and/or therapeutic result (e.g., prevention and/or treatment of a renal disorder). An effective amount of a compound of the invention may vary according to factors such as the disease state, age, sex, and weight of the individual, and the ability of the compound to elicit a desired response in the individual. Dosage regimens may be adjusted to provide the optimum therapeutic response. An effective amount is also one in which any toxic or detrimental effects of the compound are outweighed by the therapeutically beneficial effects. For any particular subject, specific dosage regimens may be adjusted over time according to the individual need and the professional judgment of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In an embodiment, the carrier is suitable for parenteral administration. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In an embodiment, the above-mentioned renal disorder is acute kidney injury. As used herein, the term "kidney injury" is equivalent to "renal injury" and these terms are used interchangeably. In another embodiment, the above-mentioned renal disorder is post-operative kidney injury or dysfunction. In an embodiment, the above-mentioned post-operative kidney injury or dysfunction results from cardiopulmonary bypass surgery for valve repair, aortic anurysm, organ transplantation, open heart surgery or coronary artery graft.

In an embodiment, the above-mentioned administration is by intravenous infusion. In a further embodiment, the above-mentioned intravenous infusion is at a rate of about 1 ng/kg/min to about 10 µg/kg/min.

In an embodiment, the above-mentioned treatment comprises the use/administration of more than one (i.e. a combination of) active/therapeutic agent. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question (e.g., a renal disorder, hypertension).

The invention further provides a kit or package comprising the above-mentioned bifunctional hormone or the above-mentioned composition, together with instructions for the prevention and/or treatment of a renal condition or hypertension in a subject.

In an embodiment, the above-mentioned subject is a mammal, in a further embodiment, a human.

MODE(S) FOR CARRYING OUT THE INVENTION

The present invention is illustrated in further details by the following non-limiting examples.

EXAMPLE 1

Preparation of the Bifunctional Hormones

Solid Phase Synthesis

The bifunctional hormones of the present invention were made using a manual solid phase peptide synthesis approach using fluorenylmethoxycarbonyl-protected alpha-amino acids with appropriate side-chain protection and Benzhydrylamine (BHA) resin (BACHEM AG) with a loading of 0.75 mmol/g. Before the coupling of amino acids, 6-aminohexanoic acid and Rink linker were coupled to the resin, the Fmoc-[9H-fluoren-9-ylmethoxycarbonyl] protected amino acid were then coupled using [2-(6-Chloro-1H-benzotriazole-1-yl)-1,1,3,3-tetramethylaminium hexafluorophosphate] (HCTU) and diisopropylethylamine (DIEA) in N,N-Dimethylformamide (DMF) for 1 hour. Fmoc deprotection was performed using 20% (v/v) piperidine in DMF for 1 hour. A general procedure for N-capping the peptides of the invention with acetyl was performed using acetic anhydride and DIEA. After completion of synthesis, peptides were cleaved from the solid phase support with simultaneous side-chain deprotection. Crude linear peptides were further purified by preparative RP-HPLC on Vydac™ C18-columns using acetonitrile gradient in 0.1% Trifluoroacetic acid (TFA). The peptides were vacuum-dried to remove acetonitrile and lyophilized from 0.1% TFA. Purity was assessed by analytical High Performance Liquid Chromatography (HPLC) and masses were determined by Matrix Assisted Laser Desorption/ionisation Mass Spectrometry (MALDI-TOF MS) analysis using a Voyager™ instrument (PerSeptive Biosystems Inc.).

Oxidative Cyclization of the Linear Peptide to Cyclic Peptide (Disulfides)

The linear peptide was dissolved in a solution of 20% DMSO/HCl 1M (v/v) at a concentration of approximately 1 mg/ml. The progress of the oxidation reaction was monitored by analytical C18 RP-HPLC. The reaction was complete after 12 h. The solution was than purified using preparative C18 RP-HPLC. Purity was assessed by analytical HPLC and masses were determined by MALDI-TOF MS analysis using a Voyager™ instrument (PerSeptive Biosystems Inc.).

Cyclization to Lactam on Resin

After assembling the linear sequence, the orthogonal protecting groups on the glutamic acid and lysine side chains, namely the Glu(γ-O-All) and Lys(ε-N-Aloc) protecting group, respectively, were removed using palladium (0) catalyst. After the removal of side chain protecting groups (confirmed by Kaiser test), the free amino and carboxyl side chains were cyclized by treating with [(7-azabenzotriazol-1-yl)oxytris-(pyrrolidino)phosphonium hexafluorophosohate] (PYAOP) in DMF. Cyclization conditions were repeated until a negative Kaiser test was obtained.

Different bifunctional hormones were synthesized and are listed below in Table III.

TABLE III

| SEQ. ID. NO: | Sequence |
|---|---|
| 29 | Nle-[E-H-F-G-G-R-Nle-D-R-I-S-K]-Y-R-<u>H-f-R-W</u>-NH$_2$ |
| 30 | <u>Ac-H-f-R-W-G-K-P</u>-M-[E-H-F-G-G-R-M-D-R-I-S-K]-Y-R-NH$_2$ |
| 31 | <u>Ac-H-f-R-W-G-K-P</u>-M-[C-H-F-G-G-R-M-D-R-I-S-C]-Y-R-NH$_2$ |
| 32 | Nle-[C-H-F-G-G-R-Nle-D-R-I-S-C]-Y-R-<u>H-f-R-W</u>-NH$_2$ |
| 33 | <u>Ac-H-f-R-W-G-K-P</u>-M-[C-F-G-G-R-M-D-R-I-G-A-Q-S-G-L-G-C]-N-S-F-R-Y-NH$_2$ |
| 34 | <u>Ac-H-f-R-W-G-K-P</u>-Nle-[C-H-F-G-G-R-Nle-D-R-I-S-C]-Y-R-NH$_2$ |
| 35 | <u>Ac-H-f-R-W-G-K-P</u>-Nle-[C-F-G-G-R-Nle-D-R-I-G-A-Q-S-G-L-G-C]-N-S-F-R-Y-NH$_2$ |
| 36 | <u>M-E-H-F-R-W-G</u>-R-R-S-S-[C-F-G-G-R-M-D-R-I-G-A-Q-S-G-L-G-C]-N-S-F-R-Y-NH$_2$ |
| 37 | <u>M-E-H-f-R-W-G</u>-R-R-S-S-[C-F-G-G-R-M-D-R-I-G-A-Q-S-G-L-G-C]-N-S-F-R-Y-NH$_2$ |
| 38 | <u>Ac-H-F-R-W-G</u>-R-R-S-S-[C-F-G-G-R-M-D-R-I-G-A-Q-S-G-L-G-C]-N-S-F-R-Y-NH$_2$ |
| 39 | <u>Ac-H-f-R-W-G</u>-R-R-S-S-[C-F-G-G-R-M-D-R-I-G-A-Q-S-G-L-G-C]-N-S-F-R-Y-NH$_2$ |
| 40 | S-L-R-R-S-S-[C-F-G-G-R-M-D-R-I-G-A-Q-S-G-L-G-C]-N-S-F-R-Y-<u>H-f-R-W</u>-NH$_2$ |
| 41 | <u>Ac-E-H-F-R-W-G</u>-R-R-S-S-[C-F-G-G-R-M-D-R-I-G-A-Q-S-G-L-G-C]-N-S-F-R-Y-NH$_2$ |
| 42 | <u>Ac-E-H-f-R-W-G</u>-R-R-S-S-[C-F-G-G-R-M-D-R-I-G-A-Q-S-G-L-G-C]-N-S-F-R-Y-NH$_2$ |
| 43 | <u>Ac-H-R-W-G-K-P-M</u>-[C-F-G-G-R-M-D-R-I-G-A-Q-S-G-L-G-C]-N-S-F-R-Y-NH$_2$ |
| 44 | <u>Ac-H-f-R-W-G-K-P-M</u>-[C-F-G-G-R-M-G-A-Q-S-G-L-G-C]-N-S-F-R-Y-NH$_2$ |
| 45 | <u>Ac-H-f-R-W</u>-S-P-K-M-V-Q-G-S-G-[C-P-G-R-K-M-D-R-I-S-S-S-G-L-G-C]-K-V-L-R-R-H-NH$_2$ |
| 46 | <u>Ac-H-f-R-W</u>-G-P-K-P-V-Q-G-S-G-[C-P-G-R-K-M-D-R-I-S-S-S-G-L-G-C]-K-V-L-R-R-H-NH$_2$ |

Ac = N-terminal acetylation
NH$_2$ = C-terminal amidation
f = D-phenylalanine
[ ] = cyclized peptide via a disulfide bridge or a lactam bridge; the amino acid to the right of "[" forms a bridge with the amino acid to the left of "]".
The underlined portion of each above sequence of the bifunctional hormone represents the first domain (α-MSH activity) and the portion that is not underlined represents the second domain (natriuretic activity).

EXAMPLE 2

Activity of the Bifunctional Hormones

The bifunctional hormone was tested on ANP receptor-expressing LLC-PK1 cells and on MCR1 receptor-expressing B16-F1 cells. Both cell types were cultured 24 hours before the stimulation, in 96-well plates, at a concentration of $1.0 \times 10^5$ cells/ml. Before stimulation, cells were starved 2 hours in DPBS only and incubated 10 min in assay buffer (DPBS containing 20 mM HEPES, 0.1% BSA and 500 µM IBMX). The dose response curve of the bifunctional hormone was done for 30 minutes with concentrations of $10^{-6}$M through $10^{-12}$M. Supernatant was collected and cAMP (B16-F1) or cGMP (LLC-PK1) was measured with a radiolabeled kit from GE Healthcare Company. Results for these experiments are presented in Table IV.

TABLE IV $EC_{50}$ of the bifunctional hormones on the production of cAMP (BC16-F1 cells) and cGMP (LLC-PK1 cells)

| SEQ. ID. NO: | Sequence | $EC_{50}$ MCR1 receptor BC16-F1 cells | $EC_{50}$ ANP receptor LLC-PK1 cells |
|---|---|---|---|
| 1 | Ac-S-Y-S-M-E-H-F-R-W-G-K-P-V-NH₂ (native α-MSH) | 0.6 nM | NT |
| 2 | S-L-R-R-S-S-[C-F-G-G-R-M-D-R-I-G-A-Q-S-G-L-G-C]-N-S-F-R-Y-NH₂ (native ANP) | NR | 3.3 nM |
| 29 | Nle-[E-H-F-G-G-R-Nle-D-R-I-S-K]-Y-R-H-f-R-W-NH₂ | NT | 1.43 µM |
| 31 | Ac-H-f-R-W-G-K-P-M-[C-H-F-G-G-R-M-D-R-I-S-C]-Y-R-NH₂ | 20.9 nM | 74.3 nM |
| 32 | Nle-[C-H-F-G-G-R-Nle-D-R-I-S-C]-Y-R-H-f-R-W-NH₂ | NR | NR |
| 33 | Ac-H-f-R-W-G-K-P-M-[C-F-G-G-R-M-D-R-I-G-A-Q-S-G-L-G-C]-N-S-F-R-Y-NH₂ | 10.4 nM | 69 nM |
| 34 | Ac-H-f-R-W-G-K-P-Nle-[C-H-F-G-G-R-Nle-D-R-I-S-C]-Y-R-NH₂ | 62.5 nM | 131.9 nM |
| 35 | Ac-H-f-R-W-G-K-P-Nle-[C-F-G-G-R-Nle-D-R-I-G-A-Q-S-G-L-G-C]-N-S-F-R-Y-NH₂ | 31.4 nM | 216.3 nM |
| 36 | M-E-H-F-R-W-G-R-R-S-S-[C-F-G-G-R-M-D-R-I-G-A-Q-S-G-L-G-C]-N-S-F-R-Y-NH₂ | 49.1 nM | 33.1 nM |
| 38 | Ac-H-F-R-W-G-R-R-S-S-[C-F-G-G-R-M-D-R-I-G-A-Q-S-G-L-G-C]-N-S-F-R-Y-NH₂ | 258.9 nM | 6.9 nM |
| 39 | Ac-H-f-R-W-G-R-R-S-S-[C-F-G-G-R-M-D-R-I-G-A-Q-S-G-L-G-C]-N-S-F-R-Y-NH₂ | 11.5 nM | 52.1 nM |
| 40 | S-L-R-R-S-S-[C-F-G-G-R-M-D-R-I-G-A-Q-S-G-L-G-C]-N-S-F-R-Y-H-f-R-W-NH₂ | 9.8 nM | 7 µM |
| 41 | Ac-E-H-F-R-W-G-R-R-S-S-[C-F-G-G-R-M-D-R-I-G-A-Q-S-G-L-G-C]-N-S-F-R-Y-NH₂ | NR | 8.9 nM |
| 42 | Ac-E-H-f-R-W-G-R-R-S-S-[C-F-G-G-R-M-D-R-I-G-A-Q-S-G-L-G-C]-N-S-F-R-Y-NH₂ | 6.0 nM | 502.4 nM |
| 43 | Ac-H-R-W-G-K-P-M-[C-F-G-G-R-M-D-R-I-G-A-Q-S-G-L-G-C]-N-S-F-R-Y-NH₂ | NR | 86.8 nM |
| 44 | Ac-H-f-R-W-G-K-P-M-[C-F-G-G-R-M-G-A-Q-S-G-L-G-C]-N-S-F-R-Y-NH₂ | 1.2 nM | NR |
| 45 | Ac-H-f-R-W-S-P-K-M-V-Q-G-S-G-[C-P-G-R-K-M-D-R-I-S-S-S-S-G-L-G-C]-K-V-L-R-R-H-NH₂ | 364.7 nM | NR |
| 46 | Ac-H-f-R-W-G-P-K-P-V-Q-G-S-G-[C-P-G-R-K-M-D-R-I-S-S-S-S-G-L-G-C]-K-V-L-R-R-H-NH₂ | 28.0 nM | NR |

NR = No response detected
NT = Not tested

EXAMPLE 3

Effect of the Bifunctional Hormone on Mean Arterial Pressure (MAP) of Rat

In order to study the in vivo pharmacology of the bifunctional hormones, their effects on MAP (e.g., hypotensive effect) were measured in a protocol involving bolus intravenous injections of incremental doses of the compounds.

Animals. Sprague-Dawley (SD) rats (male, weighing from 300 to 330 g) were obtained from Charles River Inc. Animals were maintained on standard laboratory chow under a 12:12 light:dark cycle.

Surgical preparation. The rats were anesthetized with Isoflurane 2.5% for the duration of the experiment. Animals were placed under radiant warmer to keep the temperature at 37.5° C. The carotid artery was catheterized (Polyethylene™ Tubing PE90) for continuous arterial blood pressure recording with a pressure transducer (Statham™) connected to a multichannel recorder (TA240 Gould). The right jugular vein was cannulated (Polyethylene™ Tubing PE90) for drug administration. After the surgical preparation, a stabilization period of 30 minutes was allowed to elapse before the beginning of the experimental protocol. During this period, the stability of blood pressure was assessed. The peptide was injected by intravenous bolus via the jugular vein. Doses of 10, 20, 40 and 100 µg/kg were injected. A period of 15 minutes was allowed between each dose injection.

Preparation of dosing solutions. The peptides, SEQ ID NO: 2 (native ANP, #2 in the figures) and the bifunctional hormone of SEQ ID NO: 33 (#33 in the figures) were made up fresh daily in a saline solution at concentration of 100 µg/ml. Appropriate dilutions of the peptide were made in sterile saline to give 10-100 µg/kg doses prior to injection in the jugular vein. For an infusion dose of 30 µg/kg/h of the peptides, a dilution of the stock solution (100 µg/ml) in 0.1% human serum albumin (HSA) was made and infused via an implanted catheter (PE-90) in the jugular vein at a rate of 1 ml/h until the experiment was completed.

Results. As shown in FIG. 1A, native ANP (SEQ ID NO: 2) produced a decrease in MAP even at 1 µg/kg bolus iv dose whereas the bifunctional hormone (SEQ ID NO: 33) was tolerated at a dose of up to 20 µg/kg. Therefore, the bifunctional hormone (SEQ ID NO: 33) is tolerated at a higher dose than native ANP. In order to study the effects in an infusion regimen, single doses (30 µg/kg/h) of the peptides were administered by intravenous infusion. As shown in FIG. 1B, the native ANP peptide (SEQ ID NO: 2) rapidly lowered MAP whereas continuous infusion of the bifunctional hormone (SEQ ID NO: 33) at the same dose was well tolerated.

EXAMPLE 4

Effect of the Bifunctional Hormone on Hypertension in SD Rat

BNP (Natrecor®) was approved by the FDA for lowering blood pressure in hypertensive crisis. Its natural homolog, ANP, was also shown to rapidly reduce blood pressure and is useful as a therapeutic in hypertensive crisis. Activation of renin-angiotensin system is implicated in several medical indications involving hypertension. Therefore, a rat model in which blood pressure was raised with the continuous infusion of angiotensin II was used, and the potency/efficacy of native ANP (peptide #2 in the figures) and the bifunctional hormone of SEQ ID NO: 33 (peptide #33 in the figures) to reduce blood pressure was tested following intravenous bolus injections of the peptides in SD rats.

Animals. Sprague-Dawley (SD) rats (male, weighing from 300 to 330 g) were obtained from Charles River Inc. Animals were maintained on standard laboratory chow under a 12:12 light:dark cycle.

Surgical preparation. The rats were anesthetized with isoflurane 2.5% for the duration of the experiment. Animals were placed under radiant warmer to keep the temperature at 37.5° C. The carotid artery was catheterized (Polyethylene™ Tubing PE90) for continuous arterial blood pressure recording with a pressure transducer (Statham) connected to a multichannel recorder (TA240 Gould). The right jugular vein was cannulated (Polyethylene™ Tubing PE90) for drug administration. Also, tail vein was catheterized (Blood Collection Set 25G3/4×12", Becton Dickinson) for continuous angiotensin II infusion by a perfusion pump (Harvard Apparatus). After the surgical preparation, a stabilization period of 30 minutes was allowed to elapse before the beginning of the experimental protocol. During this period, the stability of blood pressure was assessed. Hypertension was induced by an intravenous infusion of Angiotensin II (5 ug/kg/h) via the tail vein. After 30 minutes of Ang II infusion that allowed stable blood pressure, the peptide was injected by an intravenous bolus via the jugular vein. Doses of 100, 200, 300, 400 and 500 ug/kg were injected. A period of 15 minutes was allowed between each dose injection.

Preparation of dosing solutions. Angiotensin II was made up fresh daily in saline at concentration of 100 µg/ml. For the 5 µg/kg/h infusion, 30 µl of Ang II (100 µg/ml) was put in 2 ml saline for 2 h infusion (1 ml/h). Peptides (#2 and #33) were also made up fresh daily in a saline solution at concentration of 1000 µg/ml. Appropriate dilutions of the stock solution were made in sterile saline to give 100-500 µg/kg doses in an injection volume of 0.2 ml.

Figure 2:
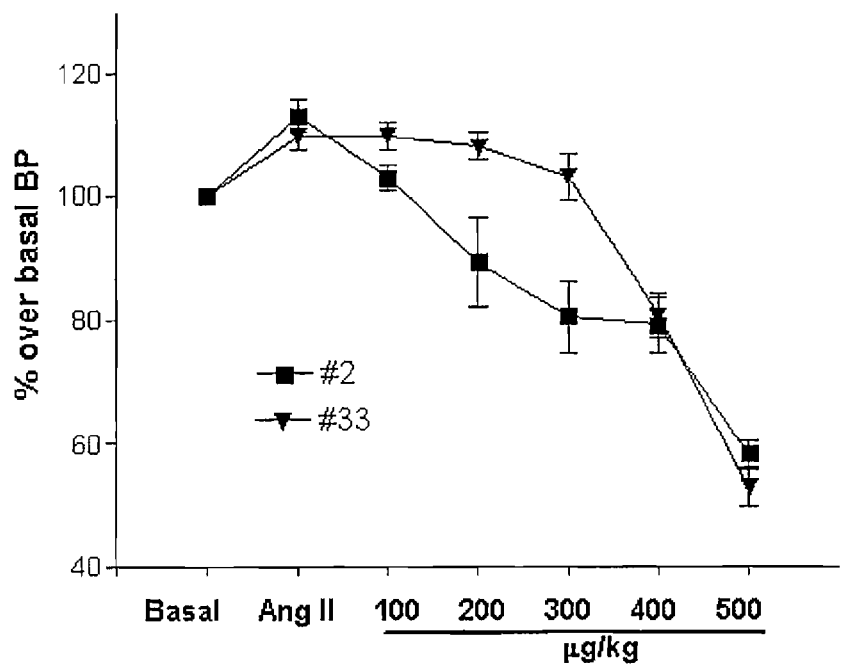
FIG. 2 shows the effect of the bifunctional hormone on hypertension in SD rat. The data were plotted as percent change from the basal blood pressure.

Results. As shown in FIG. 2, infusion of angiotensin II rapidly elevated the basal blood pressure (Bas) by about 10-15% (Ang). Bolus injections of the native ANP (#2) rapidly normalized the blood pressure at a dose of 100 µg/kg, and produced hypotension at higher doses (i.e. 200-500 µg/kg). Doses of up to 300 µg/kg of the bifunctional hormone (#33) did not induced hypotension, however at doses of 400 µg/kg and above, the bifunctional hormone had an effect similar to that of ANP.

EXAMPLE 5

Effect of Prophylactic Treatment With the Bifunctional Hormone on Acute Kidney Dysfunction Following Renal Ischemia Acute kidney injury following renal ischemia (reproduced in animal models by clamping one or both renal arteries for 30-60 min) elicits a combination of renal vascular constriction leading to reduced blood flow, epithelial injury comprising the elevation of tubular markers in the urine and apoptosis and inflammation following the secretion of cytokines such as IL-1 and infiltration of neutrophils and monocytes to the site of the injury.

Animals. Sprague-Dawley (SD) rats (male, weighing from 300 to 330 g) were obtained from Charles River Inc. Animals were maintained on standard laboratory chow under a 12:12 light:dark cycle.

Surgical preparation. The rats were anesthetized with Isoflurane 2.5% for the duration of the experiment. Animals were placed under radiant warmer to keep the temperature at 37.5° C. A blood sample (0.5 ml) was collected via tail vein artery before the renal artery clamping. Once the animal was anesthetized, placed in a supine position, a 1.5 cm flank incision was made on the right side of the abdominal wall. The right kidney was then exposed and the ureter, renal artery and renal vein were carefully dissected and ligated. The kidney was removed after cutting renal pedicle. A same incision was made on the left side of the abdominal wall. The left kidney is exposed and the renal vascular pedicle is carefully dissected. The renal vascular pedicle was then occluded by placing a vascular clip (Micro Serrefine™, Fine Science Tools) for a period of 30 or 45 minutes. This renal vascular pedicle clamping produced an acute renal artery occlusion (RAO). The kidney was inspected for ischemia as well as for good reperfusion after removing vascular clip for 2 minutes. The wound of abdominal wall was closed in two layers. The muscular layer was closed with a running 3-0 silk suture and the skin was closed with suture clips (Fine Science Tools). 21 hours after right nephrectomy and left renal artery clipping procedure, the rats were put in the metabolic cages for urine collection (in pre-weighed Tube 50 ml) for 3 hours. Urine volume was measured by weighing the tube containing urine. Then, the animals were anesthetized with Isoflurane 2.5%. Left kidney was removed and kept in formalin for future histology. Blood was collected by cardiac puncture into a heparinized syringe (3 ml) and immediately transferred into appropriately labeled tubes that contain heparin as the anticoagulant. Following collection, all blood samples were kept on ice and centrifuged for 2 min at 13000 rpm. Plasma and urine aliquots (400 µl) were removed and stored at −80° C.

Preparation of dosing solutions. Peptides (#2 and #33) were also made up fresh daily in a 0.1% HSA saline solution (33 µl of 30% HSA in 9.967 µl saline) at concentration of 100 µg/100 µl. For the 15 µg/kg/h infusion, 9 µl of peptide (100 µg/100 µl) was put in 2 ml of 0.1% HSA saline for 2 h infusion (1 ml/h).

Figure 3:
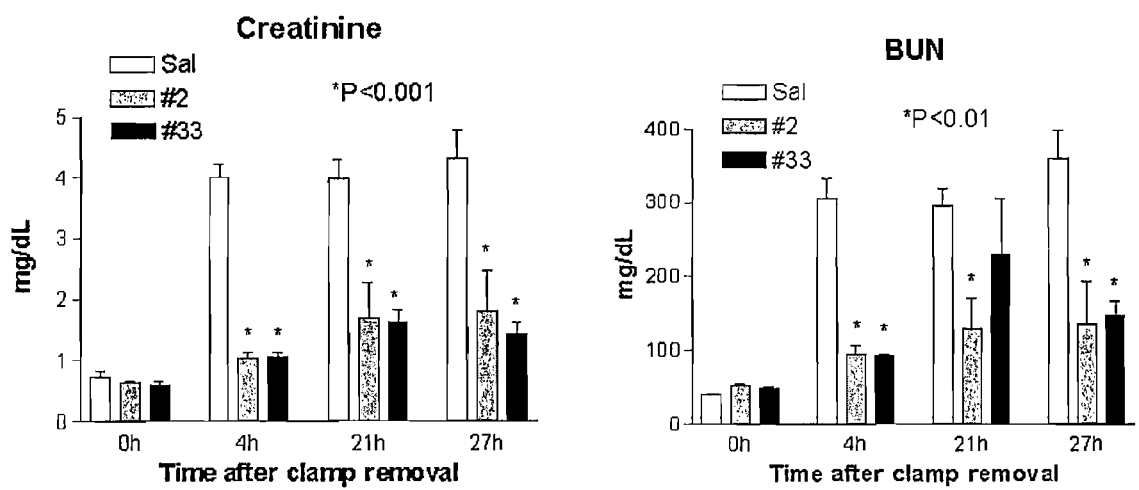
FIG. 3 shows the effect of prophylactic treatment with the bifunctional hormone on acute kidney dysfunction following renal ischemia; Peptides #2 or #33 were infused at 15 µg/kg/h for 1 h before and 1 h after renal artery clamping. Plasma creatinine and urea were determined at different times. Data were analyzed by two way ANOVA using Bonferroni test for significance against the saline-treated group (n=3 per group; sal n=6).

Results. As shown in FIG. 3, plasma creatinine and urea levels were elevated in a time-dependent fashion in the saline treated group. Both peptides significantly reduced the elevation in blood concentrations of creatinine and blood urea nitrogen (BUN) at each time point. Therefore, the bifunctional hormone (#33) is as effective as native ANP (#2) for diminishing kidney injury when used prophylactically.

EXAMPLE 6

Effect of Post-injury Treatment With the Bifunctional Hormone on Acute Kidney Dysfunction Following Renal Ischemia In order to verify if short infusions of the peptides post-injury (therapeutic treatment) would be beneficial to reduce kidney injury, peptides #2 or #33 were infused at 15 μg/kg/h for 2 h after renal artery clamp removal. Plasma creatinine and urea were determined at different times. The animal model and the dosing solutions were prepared as described in Example 5 above.

Figure 4:
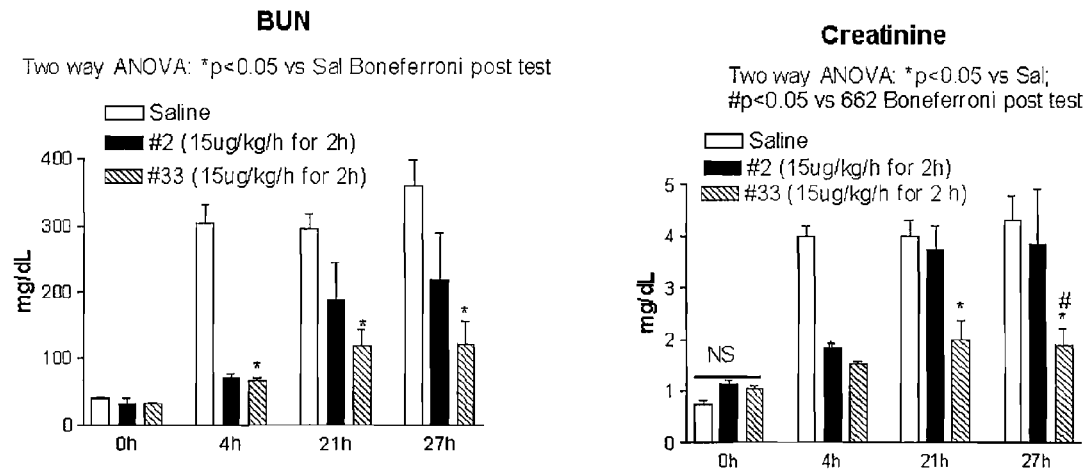
FIG. 4 shows the effect of therapeutic (i.e., post-injury) treatment with the bifunctional hormone on acute kidney dysfunction following renal ischemia. Peptides #2 and #33 were infused for 2 h after the removal of the renal clamps in the rat model of renal ischemia. Blood samples were collected at the indicated times and plasma creatinine and urea were determined. Data were analyzed by two way ANOVA using Bonferroni test for significance against the saline-treated group (n=3 per group; sal n=6)

Results. As shown in FIG. 4, plasma creatinine and BUN levels increased in the saline treated group in a time dependent manner. Both peptides prevented the rise in creatinine and BUN at 4 h, but at later time points (i.e. 21 h and 27 h), the bifunctional hormone (#33) was more effective than native ANP (#2) at reducing creatinine and BUN levels following renal ischemia.

EXAMPLE 7

Effect of Chronic Infusion of the Bifunctional Hormone on Acute Kidney Dysfunction Following Renal Ischemia In order to test the effect of chronic infusion of the bifunctional hormone on kidney function on kidney injury, peptides #2 or #33 were infused at 1.5 or 15 μg/kg/h for 24 h after renal artery clamp removal. Plasma creatinine and urea nitrogen were determined at 24 h after the injury. The experimental procedures (animal model, dosing solutions) were the same as those described in Example 5 above.

Figure 5:
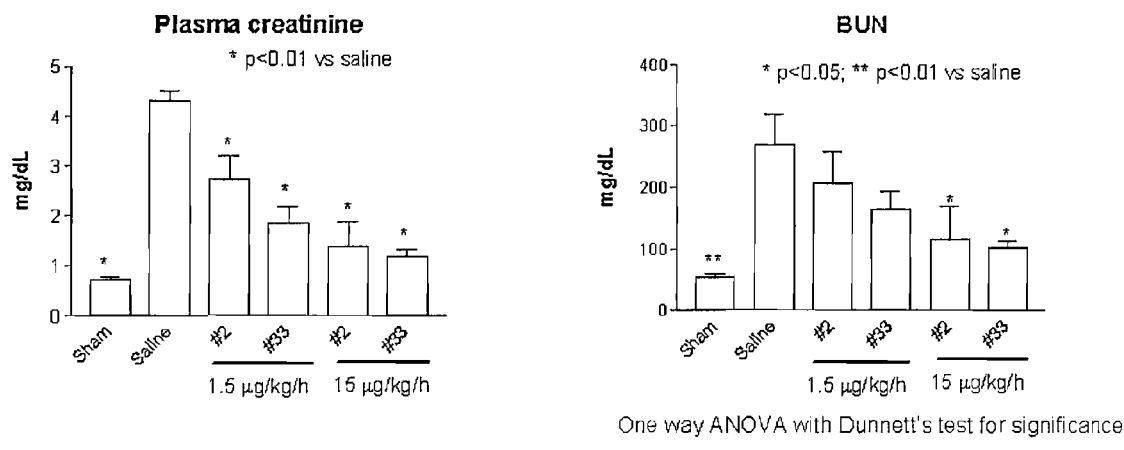
FIG. 5 shows the effect of chronic infusion of the bifunctional hormone on acute kidney dysfunction following renal ischemia. After removing the renal artery clamps, peptide #2 or #33 was infused at two doses using intraperitoneally implanted Alzet™ minipumps (2ML1; delivery rate 10 μl/h). Plasma creatinine and BUN were determined at the indicated times. Data were analyzed by two way ANOVA using Bonferroni test for significance against the saline-treated group (n=3 per group; sal n=6)

Results. Both native ANP (#2) and the bifunctional hormone (#33) reduced plasma creatinine and BUN significantly as compared to the saline-treated animals following a 24-hour infusion (FIG. 5). There was a dose-dependent reduction in the blood markers of renal ischemia with both peptides. The bifunctional hormone #33 was more effective than native ANP at ameliorating the consequences of kidney injury, as evidenced by the more pronounced reduction in creatinine and BUN levels (FIG. 5).

EXAMPLE 8

Effect of Treatment With the Bifunctional Hormone on Inflammatory and Acute Kidney Injury Markers Following Renal Ischemia Renal ischemia elicits increased expression of inflammatory markers such as IL-1, IL-18, Tumor Necrosis Factor alpha (TNF-α) and CD11b (neutrophil marker; evidence of neutrophil infiltration of the tissue) as well as tubular epithelial markers such as KIM-1, NGAL and NAG. There is considerable interest in these markers since these markers are expressed earlier than the observed rise in serum creatinine levels. Therefore, diagnosis of acute kidney injury based on the markers allows for earlier treatment of the patients which may produce better outcomes in terms of dialysis need and mortality. The effect of the bifunctional hormone #33 on the expression of inflammatory and tubular injury markers was assessed using the animal model described in Example 5.

Preparation of dosing solutions. Peptide #33 was infused for 24 h at an infusion rate of 15 μg/Kg/h using Alzet™ minipumps.

Western blotting. Fresh kidneys were rapidly dissected and homogenized with a tissue homogenizer in ice cold lysis buffer: 20 mM Tris, 135 mM NaCl, 1% NP-40™, 0.1% SDS, 10% glycerol containing Complete-Mini Protease Inhibitor Cocktail™ (Roche). Following a 15-min incubation on ice, samples were centrifuged at 13,000 rpm for 5 min at 4° C. and the supernatants containing solubilized protein extracts were collected. Protein samples (40 ug protein) were resolved on 10% SDS polyacrylamide gel electrophoresis and transferred to PVDF membranes (Amersham, Pharmacia). Non-specific binding was eliminated by incubating membranes for 1 h at room temperature in a solution of 5% non-fat milk in TBST (10 mM Tris, 150 mM NaCl, 0.2% Tween-20). Membranes were then incubated overnight at 4° C. with either of the following primary antibodies: anti-KIM-1 (1:400; RD Systems), anti-IL-1β (1:500; Calbiochem), anti-NGAL (1:500; Santa-Cruz Biotech), anti-CD11b/c (1:400; Abcam) or monoclonal anti-β-actin (0.5 Ag/ml Sigma). Membranes were subsequently washed in TBST and incubated with a peroxidase-conjugated secondary antibody (0.5 μg/ml, Amersham Pharmacia, Baie d'Urfè, QC) for 1 h at room temperature. Blots were treated with a chemiluminescent reagent (ECL™, Amersham Pharmacia) and exposed to X-OMAT™ (Kodak) imaging film.

Figure 6:
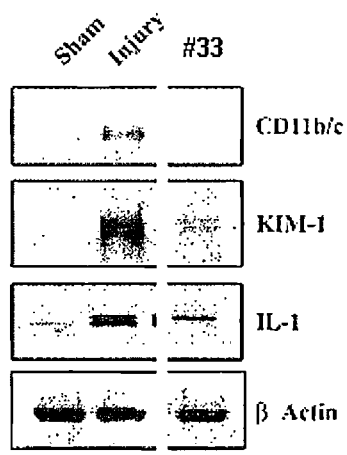
FIG. 6 shows immunochemical identification of a neutrophil marker (CD11b), a tubular injury marker (KIM-1), and an inflammatory cytokine (IL-1β) as well as a protein loading marker (β-actin) in kidneys of rats that underwent renal ischemia for 30 min. Bifunctional hormone #33 was infused at an infusion rate of 15 μg/kg/h for 24 h using Alzet™ minipumps. The proteins were identified with specific antibodies. (A) Western blot. (B) Histograms showing the relative abundance of the markers.
Figure 6:
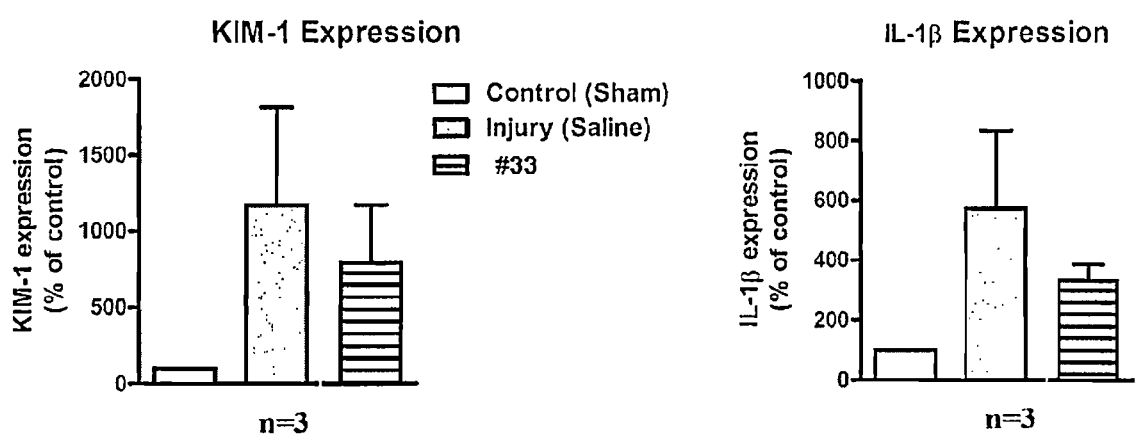

Results. As shown in FIG. 6, renal clamping for 30 min elicited strong expression of CD11b/c, KIM-1 and IL-1β (injury). Continuous infusion of the bifunctional hormone (#33) reduced the expression of the markers, thus showing its efficacy in reducing kidney injury and inflammation following ischemia.

Although the present invention has been described hereinabove by way of specific embodiments thereof, it can be modified, without departing from the spirit and nature of the subject invention as defined in the appended claims.

What is claimed is:

1. A bifunctional hormone comprising SEQ ID NO: 62 (H-f-R-W-G-K-P-M-C-F-G-G-R-M-D-R-I-G-A-Q-S-G-L-G-C-N-S-F-R-Y), wherein the C residues at positions 9 and 25 of SEQ ID NO: 62 form a disulfide bridge and wherein f is D-phenylalanine.

2. The bifunctional hormone of claim 1, wherein said bifunctional hormone consists of SEQ ID NO: 33 (Ac-H-f-R-W-G-K-P-M-C-F-G-G-R-M-D-R-I-G-A-Q-S-G-L-G-C-N-S-F-R-Y-NH$_2$), wherein the C residues at positions 9 and 25 of SEQ ID NO: 33 form a disulfide bridge and wherein Ac represents an amino terminal acetylation; NH$_2$ represents a carboxy terminal amidation; and f is D-phenylalanine.

3. A composition comprising the bifunctional hormone of claim 1 or claim 2, and a pharmaceutically acceptable carrier.

4. A method for treating acute kidney injury in a subject in need thereof, said method comprising administering an effective amount of the bifunctional hormone of claim 1 to said subject.

5. A method for treating acute kidney injury in a subject in need thereof, said method comprising administering an effective amount of the composition of claim 3 to said subject.

6. The method of claim 4, wherein said acute kidney injury is post-operative kidney injury results resulting from cardiopulmonary bypass surgery for valve repair, surgery for aortic aneurysm, organ transplantation, open heart surgery or coronary artery graft.

7. The method of claim 4, wherein said administration is by intravenous infusion.

8. The method of claim 7, wherein said intravenous infusion is at a rate of about 25 ng/kg/min to about 10 µg/kg/min.

9. A method for treating hypertension in a subject in need thereof, said method comprising administering an effective amount of the bifunctional hormone of claim 1 to said subject.

10. A method for treating hypertension in a subject in need thereof, said method comprising administering an effective amount of the composition of claim 3 to said subject.

11. The method of claim 5, wherein said acute kidney injury is post-operative kidney injury resulting from cardiopulmonary bypass surgery for valve repair, surgery for aortic aneurysm, organ transplantation, open heart surgery or coronary artery graft.

12. The method of claim 5, wherein said administration is by intravenous infusion.

13. The method of claim 12, wherein said intravenous infusion is at a rate of about 25 ng/kg/min to about 10 µg/kg/min.

14. A method for treating acute kidney injury in a subject in need thereof, said method comprising administering an effective amount of the bifunctional hormone of claim 2 to said subject.

15. The method of claim 14, wherein said acute kidney injury is post-operative kidney injury resulting from cardiopulmonary bypass surgery for valve repair, surgery for aortic aneurysm, organ transplantation, open heart surgery or coronary artery graft.

16. The method of claim 14, wherein said administration is by intravenous infusion.

17. The method of claim 16, wherein said intravenous infusion is at a rate of about 25 ng/kg/min to about 10 µg/kg/min.

18. The method of claim 4, wherein said acute kidney injury is caused by renal ischemia.

19. The method of claim 5, wherein said acute kidney injury is caused by renal ischemia.

20. The method of claim 14, wherein said acute kidney injury is caused by renal ischemia.

21. A method for reducing post-operative kidney injury or dysfunction in a subject in need of a surgery selected from cardiopulmonary bypass surgery for valve repair, surgery for aortic aneurysm, organ transplantation, open heart surgery or coronary artery graft, said method comprising administering an effective amount of the bifunctional hormone of claim 1 to said subject prior to said surgery.

22. A method for reducing post-operative kidney injury or dysfunction in a subject in need of a surgery selected from cardiopulmonary bypass surgery for valve repair, surgery for aortic aneurysm, organ transplantation, open heart surgery or coronary artery graft, said method comprising administering an effective amount of the bifunctional hormone of claim 2 to said subject prior to said surgery.

23. A method for reducing post-operative kidney injury or dysfunction in a subject in need of a surgery selected from cardiopulmonary bypass surgery for valve repair, surgery for aortic aneurysm, organ transplantation, open heart surgery or coronary artery graft, said method comprising administering an effective amount of the composition of claim 3 to said subject prior to said surgery.

24. The method of claim 21, wherein said administration is by intravenous infusion.

25. The method of claim 24, wherein said intravenous infusion is at a rate of about 25 ng/kg/min to about 10 µg/kg/min.

* * * * *